(12) United States Patent
Imai

(10) Patent No.: US 8,796,037 B2
(45) Date of Patent: Aug. 5, 2014

(54) METHOD OF DETECTION, SEPARATION AND IDENTIFICATION FOR EXPRESSED TRACE PROTEIN/PEPTIDE

(76) Inventor: Kazuhiro Imai, Tokyo (JP)

( * ) Notice: Subject to any disclaimer, the term of this patent is extended or adjusted under 35 U.S.C. 154(b) by 909 days.

(21) Appl. No.: 10/582,090

(22) PCT Filed: Dec. 13, 2004

(86) PCT No.: PCT/JP2004/018592
§ 371 (c)(1),
(2), (4) Date: Apr. 11, 2007

(87) PCT Pub. No.: WO2005/056146
PCT Pub. Date: Jun. 23, 2005

(65) Prior Publication Data
US 2008/0280316 A1  Nov. 13, 2008

(30) Foreign Application Priority Data

Dec. 11, 2003 (JP) ................................. 2003-412810

(51) Int. Cl.
G01N 21/76 (2006.01)
G01N 33/58 (2006.01)
G01N 33/68 (2006.01)

(52) U.S. Cl.
CPC .......... *G01N 33/582* (2013.01); *G01N 33/6851* (2013.01); *G01N 33/6848* (2013.01)
USPC ...................................................... 436/172

(58) Field of Classification Search
None
See application file for complete search history.

(56) References Cited

U.S. PATENT DOCUMENTS

| 6,629,046 B1* | 9/2003 | Bond et al. ...................... 702/61 |
| 6,653,625 B2* | 11/2003 | Andersson et al. ........... 250/288 |
| 6,658,739 B1* | 12/2003 | Huang .............................. 30/96 |
| 7,179,655 B2* | 2/2007 | Patricelli ...................... 436/173 |
| 2002/0099201 A1* | 7/2002 | Masuda et al. ............... 536/24.3 |

(Continued)

FOREIGN PATENT DOCUMENTS

| IN | WO 03/020832 | * | 3/2003 | .............. C09B 61/00 |
| WO | 03 002226 | | 1/2003 | |
| WO | 03 029425 | | 4/2003 | |
| WO | 03 054518 | | 7/2003 | |

OTHER PUBLICATIONS

Toyo'oka et al. New fluorogenic reagent having halogenobenzofurazan structure for thiols: 4-(aminosulfonyl)-7-fluoro-2,1,3-benzoxadiazole. Analytical Chemistry, vol. 56, pp. 2461-2464 (1984).*
Toriumi (2003) Anal Chem 75: 3725-3730.*

(Continued)

*Primary Examiner* — Chris L Chin
*Assistant Examiner* — Richard Moerschell
(74) *Attorney, Agent, or Firm* — Oblon, Spivak, McClelland, Maier & Neustadt, L.L.P.

(57) ABSTRACT

A method of detection separation and identification for expressed trace protein/peptide; and a system therefor. There is provided a method of detecting, separating and identifying a minute amount of expressed protein and/or peptide, characterized in that a fluorescent derivative of protein and/or peptide contained in a test subject sample having been labeled with a fluorescent reagent is applied to HPLC; a fluorescent fraction is collected and subjected to enzymatic hydrolysis; mass-spectrometry of the resultant fluorescence-labeled fragments and non-fluorescence-labeled fragments is carried out; and the thus obtained ion molecular weight information on each of the fragments is collated with an available protein and/or peptide fragment database to thereby accomplish a structural analysis. Further, there is provided an identification system therefor.

11 Claims, 12 Drawing Sheets

(56) References Cited

U.S. PATENT DOCUMENTS

| | | | |
|---|---|---|---|
| 2003/0036101 A1* | 2/2003 | Schrattenholz | 435/7.21 |
| 2004/0033975 A1* | 2/2004 | Fu et al. | 514/44 |
| 2004/0072251 A1* | 4/2004 | Anderson | 435/7.1 |
| 2004/0157231 A1* | 8/2004 | Meltola et al. | 435/6 |
| 2007/0065343 A1* | 3/2007 | Srinivasan et al. | 422/70 |

OTHER PUBLICATIONS

Toyooka (1984) Anal Chem 56: 2461-2464.*

Matsumoto (2001) Bioorg & Med Chem Ltr 11:605-609.*

Dunn, "Two-Dimensional Gel Electrophoresis of Proteins", Journal of Chromatography, vol. 418, pp. 145-185, 1987.

Gygi et al., "Quantitative Analysis of Complex Protein Mixtures Using Isotope-Coded Affinity Tags", Nature Biotechnology, vol. 17, pp. 994-999, 1999.

Tomoko Ichibangase, et al., "Application of Fluorogenic Derivatization-Liquid Chromatography-Tandem Mass Spectrometric Proteome Method to Skeletal Muscle Proteins in Fast Thoroughbred Horses", Journal of Proteome Research, 2009, 8 (4), 2129-2134.

Tomoko Ichibangase, et al., "Limitation of immunoaffinity column for the removal of abundant proteins from plasma in quantitative plasma proteomics", Biomed. Chromotagr. 2009; 23: 480-487.

Hiromichi Asamoto, et al., "Application of an improved proteomics method, flurogenic derivatization-liquid chromatography-tandem mass spectrometry, to differential analysis of proteins in small regions of mouse brain", Journal of Chromatography A, 1208 (2008) 147-155.

Kazuhiro Imai, et I., "A proteomics study on human breast cancer cell lines by fluorogenic derivatization-liquid chromatography/tandem mass spectrometry", Biomedical Chromatography, 22: 1304-1314 (2008).

Tomoko Ichibangase, et al., "Proteomics of *Caenorhabditis elegans* over-expressing human α-synuclein analyzed by fluorogenic derivatization-liquid chromatography/tandem mass spectrometry: identification of actin and several ribosomal proteins as negative markers at early Parkinson's disease stages", Biochemical Chromatography 22: 232-234 (2008).

Tomoko Ichibangase, et al., "A Proteomics Method Revealing Disease-Related Proteins in Livers of Hepatitis-Infected Mouse Model", Journal of Proteome Research, 2007, 6, 2841-2849.

Ichibangase T. et al. *Biomed. Chromatogr.* 2008; 22: 232-234.

Ichibangase T. et al. *J. Proteome Res.* 2007; 6: 2841-2849.

Asamoto H. et al. *J. Chromatogr. A*, 2008; 1208, 147-155.

Ichibangase, T and Imai, K. *J. Proteome Res.* 2009; 8, 2129-2134.

Imai K. et al. *Biomed. Chromatogr.* 2008; 22, 1304-1314.

* cited by examiner

METHOD OF DETECTION, SEPARATION AND IDENTIFICATION FOR EXPRESSED TRACE PROTEIN/PEPTIDE

TECHNICAL FIELD

The present invention relates to a method for detecting separating and identifying trace amounts of expressed protein and/or peptide, and more particularly to a novel method for detecting, separating and identifying trace amounts of protein and/or peptide produced in the body by expression of a gene, which enables trace amounts of protein and/or peptide to be detected and identified easily and with high sensitivity and to an identification system of the same.

The present invention is useful for providing a novel detection, separation and identification technology for proteome technology, which is expected to play an important role in the post-genome area through comprehensive analysis of expressed proteins and/or peptides.

BACKGROUND ART

An important objective in the post-genome area is the detect-ion of trace amounts of expressed protein/peptide expressed through genes and the separation and identification thereof. In the past, peptide fingerprinting following two-dimensional electrophoresis was commonly used to achieve this objective (see Non-patent Document 1). However, this method had problems with reproducibility of the method due to the complex procedure Separation and identification methods using multi-dimensional high-performance liquid chromatography (multi-dimensional HPLC), and techniques using ICAT have recently been proposed to overcome this problem (see Non-patent Document 2).

Among these methods, methods for separating and identifying protein/peptide directly by multi-dimensional HPLC have the shortcoming of requiring considerable labor and time since all proteins/peptides are processed simultaneously. In addition, methods using ICAT attempt to comprehensively analyze protein/peptide by labeling the thiol groups of thiol-containing protein/peptide with an isotope-coded affinity tag (ICAT) reagent, capturing the protein/peptide with a biotin-coupled column, subjecting all of the proteins/peptides to enzymatic hydrolysis, separating the resulting mixture of peptide fragments by HPLC, and carrying out mass spectrometry on the peptide fragments with a mass spectrometer (MS). However, since this method involves subjecting all thiol-containing protein/peptide to enzymatic hydrolysis, it has the shortcoming of fragments of non-target protein/peptide present in large amounts impairing detection and identification of target trace protein/peptide, thereby creating the need to achieve further improvement in this technical field.

[Non-Patent Reference 1] Dunn M J. Two-dimensional gel electrophoresis of proteins, J Chromatogr 1987; 418:145-185

[Non-Patent Reference 2] Gygi S. P, Rist B, Gerber S. A, Turecek F. Gelb M. H. Aebersold R. Quantitative analysis of complex protein mixtures using isotope-coded affinity tags, Nature Biotechnology 1999; 17:994-999

DISCLOSURE OF THE INVENTION

With the foregoing in view, as a result of conducting extensive research for the purpose of radically solving the above-mentioned problems of the prior art, the inventors of the present invention found that, differing from methods of the prior art, trace expressed protein and/or peptide, unable to be detected with methods of the prior art, can be detected and identified with high sensitivity by selectively separating based on fluorescence only those proteins and/or peptides which can be fluorescently labeled in a test sample, subjecting the separated proteins and/or peptides to enzymatic hydrolysis, analyzing the fractioned fluorescent fraction by mass spectrometry, collating the results with a database and applying to structural analysis, thereby leading to completion of the present invention.

An object of the present invention is to provide a method for detecting, separating and identifying the above-mentioned expressed protein and/or peptide present in trace amounts capable of detection separation and identification with high sensitivity using a simple method for measuring trace expressed proteins and/or peptides expressed through a gene.

In addition, an object of the present invention is to provide an expressed protein and/or peptide identification system for detecting, separation and identifying trace expressed protein and/or peptide with high sensitivity using the above-mentioned trace detection, separation and identification method.

Moreover, an object of the present invention is to provide a novel analysis method and means enabling detection, separation and identification at ultra-high-sensitivity of trace expressed protein and/or peptide expressed through a gene, which was unable to be detected with methods of the prior arts.

The present invention that is used to solve the above-mentioned problems is constructed from the following technical means:

(1) A method for detecting, separating and identifying an expressed trace protein and/or peptide in a test sample, wherein a protein and/or peptide in a test sample is converted to a fluorescent derivative, said fluorescent derivative is separated by fluorescence detection, the fluorescent fraction is applied to mass spectrometry or the fluorescent fraction is applied to enzymatic hydrolysis, the peptide fragments are separated, and the fractions are applied to mass spectrometry, collated with a database and provided for structural analysis to identify the expressed protein and/or peptide.

(2) The method according to above (1), wherein after converting the protein and/or peptide in the test sample to a fluorescent derivative, the fluorescent derivative is applied to HPLC to capture the fluorescent fraction, the fluorescent fraction is applied to enzymatic hydrolysis, and fluorescence-labeled fragments and non-fluorescence-labeled fragments are applied to mass spectrometry or MS/MS analysis, and the ion molecular weight data of each of the fragments thus obtained is collated with a protein and/or peptide fragment database for structural analysis.

(3) The method according to above (1), wherein (a) the protein and/or peptide in the test sample is labeled with a fluorescence reagent, (h) the fluorescent fraction is captured by subjecting the labeled protein and/or peptide to one-dimensional or two-dimensional HPLC/fluorescence detection, (c) the fluorescent fraction is applied to enzymatic hydrolysis, and (d) together with obtaining a fluorescence chromatogram by second stage HPLC/fluorescence detection of the resulting hydrolysis product, all of the peaks are applied to mass spectrometry and collated with a database for structural analysis.

(4) The method according to any of above (1) to (3), wherein a functional group-specific fluorescence reagent is added to an aqueous solution of the protein and/or peptide sample, and a surfactant and/or protein denaturing agent is optionally added to fluorescently label the protein and/or peptide.

(5) The method according to any of above (1) to (3), wherein the fluorescence-labeled protein and/or peptide sample is applied to separation means typified by ion exchange column HPLC equipped with a fluorescence detector, reverse phase partition HPLC, gel filtration HPLC or electrophoresis and the peak fraction thereof is captured while monitoring fluorescence.

(6) The method according to any of above (1) to (3), wherein the fluorescent fraction is subjected to enzymatic hydrolysis using a protease typified by various types of peptidases, trypsins and chymotrypsins.

(7) The method according to any of above (1) to (3), wherein the enzymatic hydrolysis product is applied to reverse phase HPLC equipped with a fluorescence detector to detect a fluorescence peak, and mass spectrometry or MS/MS analysis is carried out on fluorescence-labeled fragments and non-fluorescence-labeled fragments.

(8) The method according to any of above (1) to (3), wherein ion molecular weight data of each fragment obtained by applying to mass spectrometry or MS/MS analysis is collated with a protein and/or peptide fragment database by a computer to analyze the structure and identify the protein and/or peptide prior to enzymatic hydrolysis.

(9) The method according to any of above (1) to (3), wherein the test sample is a protein and/or peptide sample collected from a biological sample.

(10) The method according to any of above (1) to (3), wherein database collation is carried out using a database containing protein and/or peptide fragment data and fluorescent reagent-labeled amino acid data.

(11) A system for detecting, separating and identifying an expressed trace protein and/or peptide used in the method according to any of above (1) to (10) comprising, as constituent elements thereof, a first reactor for labeling a protein and/or peptide of a test sample with a fluorescence reagents a one-dimensional or two-dimensional HPLC equipped with a fluorescence detector for fluorescent fractionation of a fluorescent derivative labeled with the fluorescence reagent, a second reactor for enzymatic hydrolysis of the fluorescent fraction, a second-stage HPLC equipped with a fluorescence detector for fluorescent detection of fluorescence-labeled fragments of the enzymatic hydrolysis product, and one or two or more types of structural analysis devices equipped with a database containing data on amino acids labeled with the fluorescence reagent.

(12) The system according to above (11), wherein the first reactor, the one-dimensional or two-dimensional HPLC equipped with a fluorescence detector, the second reactor, and the second-stage HPLC equipped with a fluorescence detector are arranged in series.

(13) The method according to above (1) wherein a protein and/or peptide in a test sample is converted to a fluorescent derivative by using as a fluorescent derivatization reagent a compound represented by the following general formula (1):

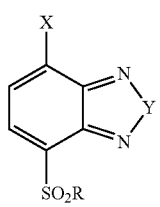

[Formula 5]

(wherein, X represents a halogen atom, Y represents C, Se or S, and R represents —NH$_2$, —NHR' (wherein, R' represents an alkyl-substituted N-alkyl group, dialkyl-substituted N-alkyl group or trialkyl-substituted N-alkyl group) or —NR"R'" (wherein, R" represents an alkyl group, and R'" represents an alkyl-substituted N-alkyl group, dialkyl-substituted N-alkyl group or trialkyl-substituted N-alkyl group)) or an isotope compound thereof, or a compound represented by the following general formula (2):

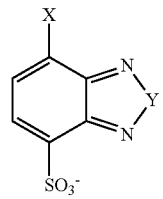

[Formula 6]

(wherein, X represents a halogen atom and Y represents Se or S), or an isotope compound thereof.

(14) The method according to above (1), wherein a protein and/or peptide in the method according to above (1) is converted to a fluorescent derivative by using a fluorescent derivatization reagent used for fluorescent derivatization which is a compound represented by the following general formula (1):

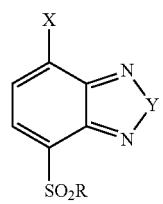

[Formula 7]

(wherein X represents a halogen atom, Y represents O, Se or S, and R represents —NH$_2$, —NHR' (wherein, R' represents an alkyl-substituted N-alkyl group, dialkyl-substituted N-alkyl group or trialkyl-substituted N-alkyl group) or —NR"R'" (wherein, R" represents an alkyl group, and R'" represents an alkyl-substituted N-alkyl group, dialkyl-substituted N-alkyl group or trialkyl-substituted N-alkyl group)) or an isotope compound thereof or a compound represented by the following general formula (2):

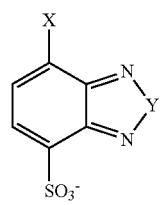

[Formula 8]

(wherein, X represents a halogen atom and Y represents Se or S) or an isotope compound thereof.

(15) A method for detecting, separating and identifying a protein and/or peptide, wherein a protein and/or peptide of a test sample is converted to a fluorescent derivative, the fluorescent derivative is separated and detected with an HPLC, enzymatic hydroxylation is carried out following fractionation, and sequence analysis and protein identification are carried out by direct mass spectrometry of the hydrolysis product.

(16) A method for detecting, separating and identifying a protein and/or peptide, wherein a protein and/or peptide in different test samples in the form of sample A and sample B is converted to a fluorescent derivative, respectively, with at least two fluorescent derivatization reagents having different fluorescence wavelengths, the fluorescent derivative is separated and detected with an HPLC equipped with a fluorescence detector, and identification is carried out by applying to quantification of each fluorescence peak either directly or collectively following fractionation and/or applying each fluorescence peak collectively to enzymatic hydrolysis followed by quantification of the hydrolysis product, or applying the hydrolysis product to HPLC-mass spectrometry.

(17) The method according to above (16), wherein each fluorescence peak is applied to quantification by HPLC either directly or collectively, and the ratio of each derivative of the protein and/or peptide in sample A and sample B is calculated.

(18) The method according to above (16), wherein the hydrolysis product is applied to quantification by HPLC, and the ratio of each derivative of the protein and/or peptide in sample A and sample B is calculated.

(19) The method according to above (16), wherein the reaction product of a first fluorescent derivatization reagent and the reaction product of a second fluorescent derivatization reagent with the protein and/or peptide in sample A and sample B are combined, applied to two HPLC capable of excitation and fluorescence detection, applied to enzymatic hydrolysis after fractionating and combining each fluorescence peak, and identification is carried out by applying the hydrolysis product to HPLC-mass spectrometry.

(20) The method according to above (16), wherein samples A and B are two types of cell, tissue or body fluid samples.

(21) The method according to above (16), wherein the protein and/or peptide is converted to a derivative with at least two fluorescent derivatization reagents having different excitation and fluorescence wavelengths among DAABD-X, DAASeBD-X and DAAThBD-X (wherein X represents Cl or F).

(22) The method according to above (21), wherein DAABD-X, DAASeBD-X or DAAThBD-X (wherein X represents Cl or F) and each isotope thereof are combined for use as fluorescent derivatization reagents having different fluorescence wavelengths.

(23) The method according to above (16), wherein simultaneously with obtaining a peptide map by directly applying an enzymatically hydrolyzed sample to mass spectrometry, the structure of a peptide portion containing cysteine is acquired by utilizing the skeleton and electric charge of the fluorescence reagent and extracting fluorescence-labeled peptide fragments with a mass spectrometry measurement unit, and the protein and/or peptide is identified on the basis thereof.

(24) An automated fractionation device capable of fractionating a protein and/or peptide derivatized with a fluorescent derivatization reagent without degrading the protein and/or peptide, at least provided with a microcolumn HPLC, microfluorescence detector, microfraction collector and automated microinjector.

(25) A high-performance, easily quantifying trace protein identification and analysis device, at least provided with a microcolumn HPLC, microfluorescence detector, microfraction collector, enzyme reaction device and automated microinjector, and optionally provided with a mass spectrometry (MS) system.

The following provides a more detailed explanation of the present invention.

In order to overcome the above-mentioned problems of the prior art, the present invention relates to a method for specifying a trace protein/peptide by 1) labeling a trace expressed protein/peptide with a fluorescence reagent, 2) carrying out first stage separation and fluoresce detection by HPLC/fluorescence detection, and 3) capturing only the fluorescent fraction (fluorescent fraction which specifically increases in a test sample as compared with a control sample), followed by enzymatic hydrolysis, separation by second stage HPLC/fluorescence detection, confirmation of the fluorescence peak, and identification of the fluorescence-labeled protein/peptide by applying to HPLC/MS. Furthermore, in the case a protein/peptide sample is of high purity the first stage separation by HPLC/fluorescence detection can be omitted. Differing from methods of the prior art, the method of the present invention is the most suited to specification of trace expressed protein peptide since it enables specific extraction, detection and identification of only those proteins/peptides capable of being fluorescently labeled.

In the present invention, samples containing all types of proteins and/or peptides collected from the body can be used for the test sample. In the method of the present invention, although trace expressed protein/peptide present in a test sample is labeled with a fluorescence reagent to obtain a fluorescent derivative, in this case, it is important to quantitatively derivatize the expressed protein/peptide by adding a functional group-specific fluorescence reagent to a protein/peptide aqueous solution, and depending on the case, adding a surfactant and/or protein denaturing agent. Namely, in the present invention, a protein and/or peptide is fluorescently labeled by adding a surfactant, and a reducing agent depending on the case, to an aqueous solution of a protein/peptide sample, adding a functional group-specific fluorescence reagent thereto, and heating as necessary. In the present invention, a nonionic, anionic, cationic or amphoteric surfactant is used for the surfactant. In addition, in the present invention, although Tris(2-carboxyethyl)phosphine or tributylphosphine is preferably used for the reducing agent, the reducing agent is not limited thereto, but rather any reducing reagent can be similarly used provided it has equivalent effects.

In the present invention, examples of the functional group-specific fluorescence reagent include, but are not limited to, amino group-specific fluorescence reagents such as 4-fluoro-7-nitro-2,1,3-benzoxadiazole (NBD-F), 5-(N,N-dimethylamino) naphthalene-1-sulfonyl chloride (DNS-CL), orthophthaldehyde (OPA), fluorescamine and 9-fluorenylmethyl chloroformate (FMOC), thiol group-specific fluorescence reagents such as ammonium 7-fluoro-2,1,3-benzoxadiazole-4-sulfonate (SBD-F), 4-(aminosulfonyl)-7-fluoro-2,1,3-benazoxadiazole (ABD-F), 4-(acetylaminosulfonyl)-7-fluoro-2,1,3-benzoxadiazole (AcABD-F), 4-fluoro-7-trichloroacetylaminosulfonyl-2,1,3-benzoxadiazole (TcAcABD-F) and monobromobimane, carboxyl group-specific fluorescence reagents used by combining 4-nitro-7-N-piperazino-2,1,3-benzoxadiazole (NBD-PZ) or 4-N,N-dimethylaminosulfonyl-7-N-piperazino-2,1,3-benzoxadiazole (DBD-PZ) with a condensing agent, and hydroxyl group fluorescence reagents such as 4-(N-chloroformylmethyl-N-methyl)amino-7-nitro-2,1,3-benzoxadiazole (NBD-COCL).

In the present inventions the protein/peptide is fluorescently labeled by heating as necessary (for example, at 30 to 100° C. and preferably 40 to 70° C. for 10 to 300 minutes and preferably 60 to 100 minutes). Subsequently, nearly the entire amount of the reaction solution is applied to ion exchange column HPLC equipped with a fluorescence detectors reverse phase partition HPLC or gel filtration HPLC, and the peak fraction is fractioned off while monitoring absorbance. In this case, fluorescence is detected by setting to a wavelength equivalent to the excitation/fluorescence wavelength of the labeled fluorescent substance. For example, in the case of being labeled with NBD-F or SBD-F, the excitation wavelength is set to 480 or 380 nm, or the excitation wavelength is set to 520 or 505 nm. In the case of ion exchange HPLC, each fraction is obtained by sequentially increasing the amount of salt such as sodium chloride, sodium sulfate, potassium perchlorate or ammonium acetate, and preferably a volatile salt such as ammonium acetate. The fraction itself or a sample in which the fraction has been concentrated and dried to a solid is applied to enzymatic hydrolysis. A suitable protease is used for the enzyme, examples of which include various types of peptidases, trypsins and chymotrypsins. At this time, enzymatic hydrolysis can be carried out on-line by connecting an enzyme column.

A portion of this solution is applied to reverse phase partition HPLC equipped with a fluorescence detector to confirm the elution position of the fluorescence label. Next, the outlet of this reverse phase partition HPLC is connected to a mass spectrometer (although any mass spectrometer can be applied, an electrospray mass spectrometer is used preferably, followed by mass spectrometry of the fluorescence-labeled fragments and non-fluorescence-labeled fragments of the enzymatic hydrolysis product (single mass spectrometry for the fluorescence-labeled fragments and additional mass spectrometry of the parent ion for the non-fluorescence-labeled fragments) or mass spectrometry/mass spectrometry (MS/MS). At this time, the fluorescence detector and mass spectrometer can be connected in series. The ion molecular weight data of each fragment obtained in this manner is then collated with a protein/peptide database connected to a computer to identify the protein/peptide prior to enzymatic hydrolysis. In this case, collation with the database in the present invention is carried out using a database containing protein and/or peptide fragment data and data on amino acids labeled with a fluorescence reagent.

In the present invention, the protein and/or peptide in the test sample containing an expressed protein and/or peptide is converted to a fluorescent derivative, this fluorescent derivative is separated with HPLC/fluorescence detector, the intensities of the fluorescence peaks are compared the fluorescent derivative of a target expressed protein and/or peptide is separated, the peak fraction of the resulting target expressed protein and/or peptide is subjected to enzymatic hydrolysis and finally the protein and/or peptide is identified by mass spectrometry or MS/MS, database collation and structural analysis. Since numerous fluorescence reagents exist for derivatizing functional portions of proteins and/or peptides such as amino groups, thiol groups, hydroxyl groups or carboxyl groups, in the present invention, a suitable reagent can be arbitrarily selected according to the purpose. As indicated in the examples to be described later, in order to derivatize, for example, a Cys-containing protein, a reagent specific for the thiol group in the form of ammonium 7-fluoro-2,1,3-benzoxadiazole-4-sulfonate (SBD-F) can be used. FIG. 1 schematically shows an example of the process of the method of the present invention. As indicated in the examples to be described later, the pancreatic polypeptides, proinsulin 2, 78 KD glucose-regulated protein, protein-binding phosphatidyl amine and thioredoxin were actually strongly induced in the islets of Langerhan two days after administration of 10 mg of dexamethasone to rats.

An important aspect in the method of the present invention is quantitative derivatization of the target expressed protein since the amount of protein in each tissue is quantified and compared between each tissue, such as between normal tissue and non-normal tissue, prior to separation by HPLC/fluorescence detection. Consequently, although a suitable surfactant is used in the present invention, when the performance of several surfactants were assessed by BSA, CHAPS was found to demonstrate high intensity than n-dodecyl-β-D-maltopyranoside (see FIG. 2). In the present invention, quantitative fluorescent derivatization is possible by setting the optimum conditions corresponding to the target expressed protein and/or peptide for pH, temperature, reaction time, additives of the derivatization reaction and the like. In the present invention, these conditions can be suitably set corresponding to the type of expressed protein/peptide, purpose of analysis and the like. According to the method of the present invention, a chromatogram of the test protein/peptide demonstrated a single fluorescence peak (see FIG. 3). In the method of the present invention, the protein/peptide detection limit is 0.2 to 6.0 fmol, a measurement curve having good linearity ($\gamma > 0.9994$) is obtained over a range of 10 to 1000 fmol under optimum conditions (see Table 1), and detection performance has been determined to be remarkable as compared with conventional methods. Table 1 shows the detection limits of various proteins/peptides as determined by fluorescence detection/HPLC.

TABLE 1

| Peptides and proteins | Molecular weight (Da) | Number of cystein residues | Detection limit (fmol) | Calibration curve (r) |
| --- | --- | --- | --- | --- |
| vasopressin | 1084 | 2 | 5 | 0.9998 |
| calcitonin | 3418 | 2 | 6 | 0.9994 |
| somatostatin | 1638 | 2 | 1.8 | 0.9999 |
| oxytocin | 1007 | 2 | 1.3 | 0.9997 |
| amylin | 3920 | 2 | 1.2 | 0.9997 |
| leptin | 16014 | 2 | 3 | 0.9999 |
| alpha1-acid glycoprotein | 21547 | 4 | 1.3 | 0.9995 |
| insulin | 5808 | 6 | 0.7 | 0.9999 |
| alpha-lactalbumin | 16228 | 8 | 0.5 | 0.9999 |
| albumin | 66385 | 35 | 0.2 | 0.9999 |

Moreover, in the present invention, the above-mentioned detection, separation and identification system comprising as constituent elements thereof a first reactor for labeling a test protein and/or peptide with a fluorescence reagent, a one-dimensional or two-dimensional HPLC equipped with a fluorescence detector for fluorescent fractionation of a fluorescent derivative labeled with the fluorescence reagent, a second reactor for enzymatic hydrolysis of the fluorescent fraction, a second-stage HPLC equipped with a fluorescence detector for fluorescent detection of fluorescence-labeled fragments of the enzymatic hydrolysis product, and one or two or more types of structural analysis devices equipped with a database containing data on amino acids labeled with the fluorescence reagent, is used for the trace expressed protein and/or peptide detection, separation and identification system used in the above-mentioned method. In this case, the above-mentioned first reactor, a one-dimensional or two-dimensional HPLC equipped with a fluorescence detector, second reactor and second-stage HPLC equipped with a fluorescence detector can be arranged in series. Suitable capacities and forms can be arbitrarily selected for these devices according to the purpose of use.

The present invention is able to convert a protein and/or peptide in a test sample into a fluorescent derivative using a compound represented by the above-mentioned general formula (1) (wherein, X represents a halogen atom, Y represents O, Se or SA and R represents —$NH_2$ or —NHR' (wherein, R' represents an N-substituted acyl group), or a compound represented by general formula (2) (wherein, X represents a halogen atom and Y represents Se or S), Moreover, the present invention is also able to provide a novel fluorescent derivatization reagent having for an active ingredient thereof any of these compounds.

Preferable specific examples of these compounds include, but are not limited to, the compounds indicated below, and any compounds can be similarly used provided they are equivalent or similar to these compounds. Compounds of the present invention can be synthesized easily in the same manner as the methods specifically described in the forthcoming examples (1) DAABD-Cl[4-(dimethylaminoethyl aminosulfonyl)-7-chloro-2,1,3-benzoxadiazole]
(2) TAABD-Cl(7-chloro-2,1,3-benzoxadiazole-4-sulfonylaminoethyl rimethylammonium chloride)
(3) DAABD-F[4-(dimethylaminoethyl aminosulfonyl)-7-fluoro-2,1,3-benzoxadiazole]
(4) TAABD-F(7-fluoro-2,1,3-benzoxadiazole-4-sulfonylaminoethyl trimethylammonium chloride)
(5) DAABSeD-Cl[4-(dimethylaminoethyl aminosulfonyl)-7-chloro-2,1,3-benzoselenadiazole]
(6) TAABSeD-Cl (7-chloro-2,1,3-benzoselenadiazole-4-sulfonylaminoethyl trimethylammonium chloride)
(7) DAABSeD-F[4-(dimethylaminoethyl aminosulfonyl)-7-fluoro-2,1,3-benzoselenadiazole]
(8) TAABSeD-F(7-fluoro-2,1,3-benzoselenadiazole-4-sulfonylaminoethyl trimethylammonium chloride)
(9) DAABThD-Cl[4-(dimethylaminoethyl aminosulfonyl)-7-chloro-2,1,3-benzothiadiazole]
(110) TAABThD-Cl(7-chloro-2,1,3-benzothiadiazole-4-sulfonylaminoethyl trimethylammonium chloride,
(11) DAABThD-F[4-(dimethylaminoethyl aminosulfonyl)-7-fluoro-2,1,3-benzothiadiazole]
(12) TAABThD-F(7-fluoro-2,1,3-benzothiadiazole-4-sulfonylaminoethyl trimethylammonium chloride)

In the present invention, for example, SBD-X, SBSeD-X, SBThD-X, DAABD-X, TAABD-X, DAABSeD-X, TAABSeD-X, DA-ABThD-X, TAABThD-X (provided X represents Cl or F) and isotopes thereof are provided as fluorescent derivatization reagents. All of these compounds can be synthesized in the same manner as in the case of the compounds indicated in the forthcoming examples. In addition, in the present invention, the chain length of side chain alkyl group of compounds represented by the above-mentioned general formula (1) can be arbitrarily changed. In the present invention, two or more of these compounds can be used in combination by utilizing differences in fluorescence wavelengths and retention times during HPLC separation. Elution from an HPLC becomes slower in the order of, for example, DAABSeD-F<DAABD-Cl or DAPABSeD-F (side chain alkyl group: propyl group)<DAPABD-Cl. In addition, additional trace detection is possible by using each of the isotopes of the above-mentioned compounds.

In the present invention, two protein samples, for example, of the same source but different histories, can be compared easily and simultaneously by using at least two fluorescent derivatization reagents having different fluorescence wavelengths. For example if one protein is from a sample of an ill patient while the other protein is from a healthy person, or in specimens of a single cell or tissue, if one protein is from a sample treated with a reagent while the other protein is from an untreated sample, and the proteins are simultaneously compared based on the same chromatogram, each derivative of the protein and/or peptide derivatized with each fluorescent derivatization reagent can be easily and accurately quantified, thereby realizing simultaneous measurement and comparison of the profiles of proteins and/or peptides in two samples.

In the present invention, an automated fractionation device is provided capable of fractionating a protein and/or peptide derivatized with a fluorescent derivatization agent which is at least provided with a microcolumn HPLC, microfluorescence detector, microfraction collector and automated microinjector. In addition, in the present invention, a high-performance, easily quantifying trace protein and/or peptide identification device is provided which is at least provided with a microcolumn HPLC, microfluorescence detector, microfraction collector, enzyme reaction device and automated microinjector, and optionally provided with a mass spectrometry (MS) system.

The present invention fluorescently labels, for example, a trace phosphoprotein or glycoprotein with a fluorescent derivatization reagent, followed by high-performance separation and detection with a microcolumn HPLC and fluorescence detector as protein while maintaining the modified phosphorylated portion and sugar bond portion, and fractionation with a microfraction collector. Enzyme is then added thereto to enzymatically hydrolyze the labeled protein followed by direct application of the hydrolyzed sample to mass spectrometry. Identification, including, for examples the modified portion of the modified trace protein following translation, is then carried out using database search software based on the resulting peptide map and fluorescence-labeled peptide map data. Since the technique of the present invention combines fluorescence detection and microcolumn HPLC it is able to, for example, identify protein present in extremely trace amounts, and extract and analyze modified protein following translation without degradation. Consequently, in addition to being able to accurately obtain data on phosphorylation sites and sugar bonding sites, the present invention allows said protein to be accurately identified thereby offering an advantage not found in analytical techniques of the prior art. The analytical technique of the present invention is expected to be widely used in the fields of bioscience and pathological chemistry, and is able to contribute to diagnosis and treatment of disease, and maintaining human health.

The present invention demonstrates the effects consisting of: 1) being able to detects separate and identify expressed protein and/or peptide expressed through a gene with high sensitivity using a simple method and means, 2) being able to detect, separate and identify trace expressed protein and/or peptide, unable to be detected with methods of the prior art, with high sensitivity and in a short period of time by using the methods of the present invention, 3) being able to provide a system for detecting, separating and identifying trace amounts of trace expressed protein and/or peptide used in the above-mentioned detections separation and identification method, and 4) being useful for providing proteome platform technology.

BEST MODE FOR CARRYING OUT THE INVENTION

Although the following provides a detailed explanation of the present invention based on examples thereof, the present invention is not limited by the following examples.

Example 1

Separation and Identification of Proteins/Peptides Containing Thiol Islets of Langerhans in Rat Pancreatic Tissues

(1) Derivatization of Proteins/Peptides Containing Thiol in Islets of Langerhans The islets of Langerhans were solubilized by adding 50 μl of a 6 M guanidine chloride dissolved in 0.1 M boric acid buffer (pH9.0), and 50 μl of each 17.5 mM TCEP, 17.5 mM SBD-F, 10 mM EDTA and 50 mM CHAPS dissolved in 6 M guanidine chloride solution were added thereto respectively, and were mixed. The mixture was reacted at 40° C. for 3 hr to derivatize them.

(2) Primary Separation Using Ion Exchange HPLC

The above reaction solution was subjected to ion exchange column, and fluorescence proteins/peptides were eluted by NaCl gradient (0, 0.04, 0.08, 0.12 and 0.3 M) to separate 5 fractions. The detection of fluorescence proteins/peptides was performed by fluorescence of SBD skeleton. HPLC conditions are shown below.
(HPLC Conditions)
Column: TSKgel DEAE-5PW 7.5×75 mm (Toso)
Guard column: C8-300-S 54.0×10 mm (YMC)
Mobile phase: Gradient elution (0-5 min: C100%, 5-15 min: A100%, 15-25 min: A87% B13%, 25-35 min A73% B27%, 35-45 min: A60% B40%, 45-55 min: B100%)
A: 5 mM trishydrochloric acid buffer (pH8.0)/acetonitrile (50:50)
B: 5 mM Ttrishydrochloric acid buffer (pH8.0)/acetonitrile (50:50)
(containing 0.3 M NaCl)
C: 5 mM trishydrochloric acid buffer (pH8.0)
Temperature of column: Room temperature (about 25° C.)
Flow rate: 0.5 ml/min
Detection: Ex380 nm, Em505 nm
Amount of injection 200 μl

(3) Secondary Separation Using Reverse HPLC

Each fraction mentioned above was concentrated, and after evaporating acetonitrile, was subjected to reverse column, and the peptides and proteins were eluted with gradient elution of acetonitrile. The detection of proteins/peptides was monitored by fluorescence of SBD skeleton. HPLC conditions are shown below
(HPLC Condition)
Column Capsule pack C8 SG300 2.0×100 mm (Shiseido)
Mobile phase: Gradient elution (0→60 min: B40%→100%)
A: 0.05% trifluoroacetic acid
B: 0.05% trifluoroacetic acid/acetonitrile (40:60)
Temperature of column: Room temperature (about 25° C.)
Flow rate: 0.2 ml/min
Detection: Ex380 nm, Em505 nm
Amount of injection: 50 μl

(4) Enzyme Treatment

Each peak fraction of HPLC was put into a tube, and after adding 0.5 μL of 0.5 M ammonium hydrogen carbonate solution to neutralize it, was concentrated to evaporate acetonitrile. 10 μL of 20 μg/mL trypsin (Promega) and 10 μL of 10 mM calcium chloride were added to the residue (about 80 μL) respectively, and was incubated at 37° C. for 2 h, and then was used as sample for HPLC-MS/MS analysis.

(5), Identification of Proteins/Peptides using MS/MS Analysis

The above sample was subjected to reverse HPLC, and performed MS/MS analysis by electrospray method. HPLC conditions are shown below. The identification of proteins/peptides were performed using NCBI as database, MASCOT as search engine.
(HPLC Conditions)
Column: Cadenza TC-Cl18 2.0×100 mm (Imtak)
Mobile phase: Gradient elution (0→30 min: B20% 100%)
A: 0.1% formic acid
B: 0.1% formic acid/acetonitrile (50:50)
Temperature of column: Room temperature (about 25° C.)
Flow rate: 0.2 ml/min
Mode of measure: positive
Range of measure: 500-3000 m/z
Amount of injection: 50 μl About 130 peaks of proteins/peptides were separated by the above method. Among them about 50 proteins/peptides were identified (Table 2, FIG. 6).

TABLE 2

| Peak no. | Ratio (Dex/Control) | Protein | Mw | Database accession no. |
|---|---|---|---|---|
| 12 | 0.5 | protein P31 | 13284 | CSRT31 |
| 15 | 0.4 | dnaK-type molecular chaperone hsp72-psl | 70884 | S31716 |
| 24 | 2.1 | pancreatic polypeptide | 10968 | NP_036758 |
| 29 | 0.5 | insulin 2 | 5797 | NP_062003 |
| 30 | 6.0 | proinsulin 2 | 12331 | NP_062003 |
| 36 | 1.9 | 78 KD glucose-regulated protein | 72302 | P06761 |
| 61 | 1.8 | phosphatidylethanolamine binding protein | 20788 | NP_058932 |
| 121 | 1.8 | thioredoxin | 12854 | NP_446252 |

Example 2

The derivatized BSA with SBD-F was digested with trypsin by the process as depicted in FIG. 1, the resulting peptides mixture was separated by reversed phase liquid chromatography (RPLC), and detected by fluorescence detector. Then, each peptide was subjected MS/MS analysis by ESI mass spectromometer. Theoretically, by trypsin digestion, BSA should generate 25 Cys-containing peptides and 35 non-Cys-containing peptides of more than 4 amino acid residue. In the present Example, more than 27 fluorescent peptides were detected fluorometically so that the quantitative derivatization has been performed (FIG. 4, A).

Eleven Cys-containing peptides and 17 non-Cys-containing peptide were detected in the mass chromatogram (FIG. 4, B). FIG. 5 shows the tandem mass spectrum derived by collision-induced dissociation (CID) of the $(M+2H)^{2+}$ precursor, m/z=873.4 (marked with an arrow in FIG. 4).

Database-searching with MASCOT, which adopts probability-based protein identification algorithm, with the CID spectrum from all of the peptide fragments identified expectedly the protein as BSA significantly (score: 139).

Example 3

The applicability of the method was tested for rat pancreas with or without dexamethasone (Dex) administration.

Dex induces type 2 diabetes, a predominant type in human diabetes, through the increase in the hepatic glucose production and induction of insulin resistance. Actually, at 24 h after the Dex treatment, the blood glucose levels reached 209.8 mg/dL, which were significantly above the pretreatment value of 118.3 mg/dL (p<0.05). In the present Example, islet of Langerhans (around 60 islets) were collected from the rat pancreas treated with or without Dex for two days and derivated with SBD-F. An important aspect for the application of the method to biological samples is the isolation of a target protein(s) by HPLC from the protein mixture. In the present Example, the fluorescent proteins were first separated via ion exchange chromatography (IEC) on the basis of varieties of negative changes generated by SBD-F and amino acids moieties.

IEC was performed with the stepwise sodium chloride gradient elution (0, 0.04, 0.08, 0.12 and 0.3 M NaCl) and the fluorescent protein mixtures were separated into the five different fractions. Then, each fraction was further separated by reversed-phase liquid chromatography (RPLC) on the basis of their varying hydrophobicities. The peak capacity (A theoretical measure of the performance of HPLC as n=L/4σ), where L is the total time over the analysis and 4σ is peak width) in the present experiment was calculated 40 per each RPLC fraction and the sum of the peak capacity for the five steps of the IEC-RPLC method was approximately 200. In the present Example, there were almost 3-50 peaks in each RPLC cycle, and the total peaks were 129 (FIG. 6).

In order to detect the low-abundant proteins, the peak capacity was increased by increasing the gradient steps for IEC. The entire fluorescent peaks on the RPLC chromatograms obtained from the control and Dex treated rat were compared. Consequently, 4 fluorescent peaks were found to be increased more than 1.8 and 3 fluorescent peaks decreased about one-half by Dex treatment (Table 2). Table 2 shows the changed profile of the expressed proteins 2 days after the administration of Dex. These proteins (target protein(s)) were isolated separately by a wide pore RPLC (30 nm pore diameter) and digested with trypsin to each peptide mixture. The every peptide mixture were subjected to the conventional pore RPLC (10 nm pore diameter) with MS/MS. By database-searching algorithm, the increased peaks, two days after Dex treatment, were identified as pancreatic polypeptide, proinsulin 2, 78 KD glucose-regulated protein, phosphatidylethanolamine binding protein and thioredoxin respectively, and the decreased peaks were identified as protein P31, dnaK-type molecular chaperone hsp72-psi and insulin 2 respectively.

Example 4

In this example, novel fluorescence derivatization reagents were synthesized by following formula 9 (1) and (2).

[Formula 9]

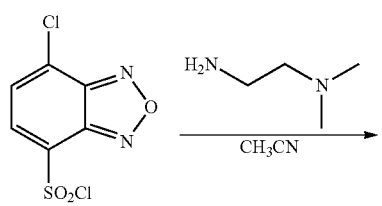

(1)

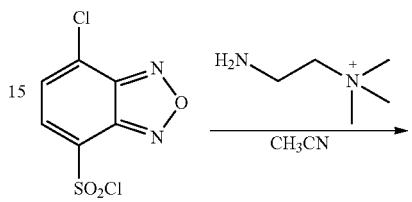

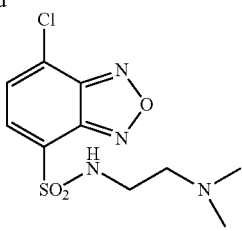

DAABD-Cl (2)

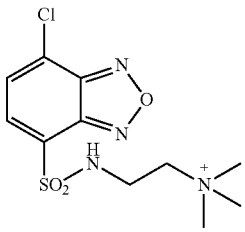

TAABD-Cl (1) Synthesis of DAAB-Cl 4-chlorosulfonyl-7-chloro-2,1,3-benzoxadiazole (CBD-Cl) (126.53 mg) was dissolved in CH$_3$CN, N,N-dimethylethylenediamine and triethylamine were added thereto. The mixture was stirred at room temperature for 10 min, the reaction mixture was evaporated to dryness under reduced pressure, and the residue was chromatographed on silica gel column (H$_2$Cl$_2$) to afford 4-(dimethylaminoethylaminosulfonyl-7-chloro-2,1,3-benzoxadiazole 5DAABD-Cl) (120.2 mg, 87.4%).

The confirmation data of the obtained compound is shown as follows.

$^1$H-NMR (CD$_3$OD): 7.94 (1H, d, J=7.5), 7.65 (1H, d, J=7.5), 3.06 (2H, t, J=6.7), 2.30 (2H, t, J=6.7), 2.02 (6H, s) ESI-MS: m/z 305 (M+H)$^+$ (2) Synthesis of TAABD-Cl 4-chlorosulfonyl-7-chloro-2,1,3-benzoxadiazole (CBD-Cl) (126.53 mg) was dissolved in CH$_3$CN, aminoethyle trimethylammonium chloride dissolved in H$_2$O and triethylamine were added thereto. The mixture was stirred at room temperature for 20 min, the reaction mixture was evaporated to dryness under reduced pressure, and then was dissolved in 0.1% trifluoroacetic acid (TFA), and was separated using ODS column, and was purified to remove SBD-Cl (formula 10) on a negative ion exchange column, and then was evaporated under reduced pressure to afford 7-chloro-2,1,3-benzoxadiazole-4-sulfoneaminoethyl trimethylammonium chloride (TAABD-Cl) (127.2 mg, 58.8%).

The confirmation data of the obtained compound is shown as follows.

$^1$H-NMR (CD$_3$OD): 8.01 (1H, d, J=7.3), 7.69 (1H, d, J=7.3), 3.46-3.48 (4H, m), 3.12 (9H, s). ESI-MS: m/z 319 (M)$^+$

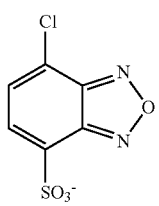

[Formula 10]

Example 5

In this example, the reactivity of the novel fluorogenic derivatization reagents was investigated.

Comparison of DAABD-Cl and TAABDD-Cl with SBD-F

100 µL of mixture of 10 µM of reduced type of glutathione, cysteine, and homocysteine in 0.10 M boric acid buffer (pH 9) was mixed with 100 µL of DAABD-Cl or TAABD-Cl in acetonitrile, and the mixture was reacted at 40° C., pH 9, for 10~120 min. The reaction of the mixture was stopped with 0.1% formic acid and then the obtained product was analyzed using HPLC.

The relation of incubation time of fluorogenic derivatization and fluorescence intensity (left figure: DAABD-Cl, right figure: TAABD-Cl) is shown in FIG. 7.

Since SBD-F requires 120 min for the derivatization reaction at 40° C., it can be conducted that DAABD-Cl requires 10~20 min, TAABD-Cl requires 20~30 min. Therefore, it is preferable that the reaction time in the case of DAABD-Cl is 20 min and the reaction time in the case of TAABD-Cl is 20~30 min.

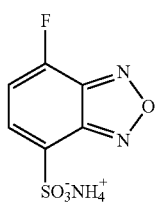

[Formula 11]

(2) Sensitivity of Novel Fluorogenic Derivatization Reagents in MS Detection

The sample prepared in the above (1), were detected by LC-MS, and the relative intensities of the samples were compared with that of the sample being not labeled with the fluorogenic derivatization reagents and the sample derivatized with SBD-F.

The relative intensities of the samples were shown in Table 3, when the ratios of intensities of underivatized cystein, homocysteine, GHS were respectively. It was revealed that DAABD-Cl was more sensitive reagent in MS detection. Since mobile phase is acidic, it is considered that the derivatized sample with DAABD-Cl is charged with positive and is soluble in water.

TABLE 3

|  | SBD-F | DAABD-Cl | TAABD-Cl |
| --- | --- | --- | --- |
| cysteine | 23 | $3.0 \times 10^3$ | $2.0 \times 10^3$ |
| homocysteine | 4.0 | $2.3 \times 10^2$ | $1.6 \times 10^2$ |
| GSH | 1.6 | $2.1 \times 10^2$ | $1.7 \times 10^2$ |

Example 6

(1) Application of TAABD-Cl to Peptides

10 µM of each peptide sample mentioned below, and 50 µL of 17.5 mM TAABD-Cl, 10 mM EDTA, 50 mM CHAPS (surfactant) and 2.5 mM TCEP (reducing agent) were mixed, and reacted at 40° C., pH9.0, for 30, 60, 90, and 120 min respectively. Each regents was dissolved in 0.10 M boric acid buffer (pH9.0) containing 6.0 M HCl guanidine (protein denaturating agent). Obtained peptides derivatized with TAABD were analyzed using HPLC.
  1. vasopressin
  2. oxytocin
  3 somatostatin
  4. amylin(rat)

FIG. 8 shows the relation of the reaction time with TAABD-Cl and fluorescence intensity.

The amount of product increased until 60 min of the reaction time. After the reaction was stopped, the product was stored under the cooling condition of ice, and was not degradated for 48 h when stored at −20° C.

(2) Detection Limits of DAABD Derivatives

10 µM of each peptide and protein sample of 10 types as shown in Table 4, and 50 µL of 2.5 mM TCEP, 17.5 mM DAABD-Cl, 10 mM EDTA and 50 mM CHAPS were mixed respectively, and reacted at 40° C., pH9.0 for 30 min. Each reagent was dissolved in 0.10 M boric acid buffer (pH9.0) containing 6.0 M HCl guanidine. Obtained peptides and proteins derivatized with DAABD were analyzed using HPLC, and detection limits thereof were compared with that of SBD-F.

TABLE 4

Detection limits of each peptide and protein by HPLC-fluorescence detection method

| Peptides and proteins | Moleculer weight (Da) | Number of cystenyl residues | Detection limit (fmol) | |
| --- | --- | --- | --- | --- |
| | | | DAABD-Cl | SBD-F |
| vasopressin | 1084 | 2 | 7.0 | 5.0 |
| oxytocin | 1007 | 2 | 4.5 | 1.3 |
| somatostatin | 1638 | 2 | 20 | 1.8 |
| calcitonin | 3418 | 2 | 5.0 | 6.0 |
| amylin (rat) | 3920 | 2 | 4.5 | 1.2 |
| insulin | 5808 | 6 | 2.2 | 0.7 |
| alpha1-acid glycoprotein | 21547 | 4 | 8.5 | 1.3 |
| alpha-lactalbumin | 16228 | 8 | 3.5 | 0.5 |
| albumin (BSA) | 66385 | 35 | 0.5 | 0.2 |
| leptin | 16014 | 2 | 30 | 3.0 |

(3) Identification of Peptides and Proteins Derivatized with DAABD

In the compounds derivatized in the above (2), vasopressin, oxytocin, somatostatin, calcitonin, and amylin were identified using LC-MS. The molecular weights of them are shown as follows.

m/z 541.8 $(M+3H)^{3+}$[DAABD-vasopressin]
516.0 $(M+3H)^{3+}$[DAABD-oxytocin]
726.6 $(M+3H)^{3+}$[DAABD-somatostatin]
989.9 $(M+4H)^{4+}$[DAABD-calcitonin]
892.8 $(M+5H)^{5+}$[DAABD-amylin]

The molecular weight of each derivative is the molecular weight of the compound in which DAABD is attached to two cysteine residues of each protein, it is revealed that in the derivatization reaction with DAABD-Cl, the reagents were reacted with the both two thiol residues and the S—S bonds between cysteine residues of these peptides were reduced according to the result of the detection of multivalent ion peak.

Further, in the case of proteins, since it is needed to digest them to peptides by enzyme, the digestion of the proteins by trypsin, the LC-MS/MS detection, and database search by MASCOT were performed and as the result, the proteins were identified together with the determination of the amino acid sequences of the peptides containing no cysteine Example 7

Synthesis of SBSeD-F

3-Fluoro-o-phenylenediamine was prepared according to the methods that nitration of 2-fluoroacetanilide gave 1-acetylamine-2-nitro-6-fluorobenzene, which was deacylated to 2-fluoro-6-nitro aniline, and then hydrogenated to 3-fluoro-o-phenylenediamine using paradium-on-charcoal catalyst.

A hot solution of seledium dioxide in ethanol was added to a hot solution of the 3-fluoro-o-phenylenediamine (60 mg, 0.48 mmol, in ethanol and the mix true was heated for 30 min. Purification by chromatography on a silica gal column eluting with dichloromethane as an eluent gave 4-fluoro-2,1,3-benzoslenadiazole as a white powder 88 mg. Confirmed data of the obtained chemical compound is shown as follows.

mp. 129° C., NMR (methanol-$d_4$): δH7.55 (1H, d J=9.2), 7.41 (1H, m), 7.06 (1H, m), ESI-MS: m/z 202.8 [(M+H)].

4-Fluoro-2,1,3-benzoselenadiazole thus obtained was dissolved in fuming sulfuric acid (60%) and refluxed at 130° C. for 3 hr. The solution was rooled, slowly poured into cold water (30 ml) and neutralized with 28% ammonium hydroxides. The neutral solution was added by 100 ml of ethanol, and the filtrate was evaporated to dryness. The residue was dissolved in water (11.0 ml) and further purified by HPLC under the following conditions. Namely, 100 μl aliquot of the residue was injected to the HPLC column. HPLC column: TSK-gel ODS-120T, 150×4.6 mmi.d., Tosoh, eluent: distilled water, the flow rate of the mobile phase 0.5 ml/min, the detection was made at 2008 nm. The fraction corresponding to SBSeD-F was collected and evaporated to give white powder. Confirmed data of the obtained chemical compound is shown as follows.

m.P.>300° C., NMR (methanol-$d_4$): δH7.97 (1H, dd, J=7.6, J=5.4), 7.11 (1H, dd, J=7.6, J=10.1), ESI-MS: m/z 280.8 [(M–H)].

Example 8

Synthesis of SBThD-F

4-Fluoro-2,1,3-benzothiadiazole was synthesized according to the method in which N-thionylaniline (0.49 g, 3.5 mmol) was added to a solution of the 3-fluoro-O-phenylene diamine (200 mg, 1.6 mmol) in foluen (2 ml) The reaction mixture was heated at 100-120° C. for 4 hr. After the solvent was filtered off, the residue was dissolved in dichloromethane and the solution was washed with 10% HCl solution and water, successively. The organic layer was dried and evaporated to dryness. Purification by chromatography on a silica gel column with chloroform as an eluent gave 4-fluoro-2,1, 3-benzothiadiazole as pal yellow oil. Confirmed data of the obtained chemical compound is shown as follows.

NMR (methanol-$d_4$) δH7.69 (1H, d, J=8.9) 7.50 (1H, m), 7.20 (1H, m), ESI-MS: m/z 154.9 [(M+H)].

Thus obtained 4-fluoro-2,1,3-henzothiadiazole (30 ml) dissolved in fuming sulfuric acid (60%) was refluxed at 130° C. for 3 hr. Then the solution was cooled, slowly poured into cold water (30 ml) and neutralized with 28% ammonium hydroxide. The neutral solution was added by 100 ml of ethanol, and the filtrate obtained was evaporated to dryness. The residue was dissolved in water (1.0 ml) and further purified by HPLC with the following conditions. The fraction corresponding to SBThD-F was collected and evaporated to give a white powder. Confirmed data of the obtained chemical compound is shown as follows.

decomp, 265° C., NMR (methanol-$d_4$): δH8.06 (1H, dd, J=7.9, J=4.9), 7.11 (1H, dd, J=7.9, J=9.8), ESI-MS: m/z 232.8 [(M–H)].

[Formula 12]

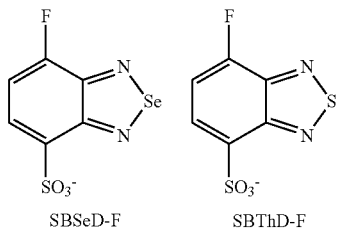

SBSeD-F　　　　SBThD-F

Example 9

(1) Fluorescence spectra of cpteine derivatives 500 μl portion of each fluorescent reagent solution (4 mM) of said SBSeD-F, SBThD-F or SBD-F in 0.1M borate buffer (pH9.0) containing 1 mM EDTA was mixed with the same volume of the solution of cysteine (0.4 mM) in 0.1M borate buffer (pH9.0). The mixture was allowed to stand at 60° C. for 8 h. After the reaction, the reaction mixture was injected onto a HPLC, the fractions corresponding to each cysteine derivatives were collected and their fluorescence spectra were measured.

Reactivity of SBSeD-F and SBThD-F to Cysteine

A 500 μl portion of 0.1 M borate buffer solution (pH9.0 or pH10) containing 4 mM each reagent, SBSeD-F, SBTHD-F or SBD-F and 1 mM EDTA was mixed with the same volume of the solution of cysteine (0.4 mM) in 0.1 M borate buffer (pH9.1 or pH10). The reaction mixture was injected onto HPLC and the reaction at 60° C. was monitored.

(2) Result

A soluble reagent such as SBD-F increases the solubility of the derivatives in aqueous media owing to its sulfonic acid residue, resulting in the less adsorption or precipitation of the derivatives. Accordingly, the derivatives with SBD-1 of the comparatively hydrophobic peptides such as insulin were well eluted from a reversed phase column and sensitively detected. In this Example, further, as fluorescent reagents bearing benzoselenadiazole or benzothiadiazole skelton, SBSeD-F and SBThD-F were synthesized and their reactivity to cysteine and the fluorescence properties of the derivatives were studied.

The maximum excitation (Rex) and emission wavelength (λem), and the retention times of the derivatives were summarized in Table 5. Every mass SBSeD-F (m/z 381.9), SBThD-F (m/z 334.0) and SBD-F (m/z 318.0) were coincided with the theoretical mass numbers (382.0, 334.0 and 318.0, respectively). The maximum excitation wavelengths of the derivatives with SBSeD-F (340 nm) and SBThD-F (315 nm) were shorter than that with SBD-F (365 nm), While the maximum emission wavelength of the derivative with SBSeD-F (542 nm) was longer than those with SBThD-F (517 nm and SBD-F (514 nm). Although SBSeD-F itself afforded little fluorescence, SBThD-F gave small fluorescence (λex; 350 nm, λem; 424 nm). The retention times ($t_R$) of the cysteine derivatives with SBSeD-F, SBTThD-F and SBD-F on a reversed phase column ($C_{18}$) using a mobile phase of ph 2.0 were 4.5, 5.3 and 4.8 min, respectively. Considering the retention times, SBSeD-F should be the most hydrophilic fluorogenic reagent among them.

In the case of SBD-F, the optimum reaction condition was to be 60° C. at pH 9.5 for 1 h, the reactivities of SBSeD-F and SBThD-F were low as compared with SBD-F and the fluorescence intensities increased gradually up to 8-24 h (FIGS. 9 and 10), the reaction did not reach maximum even after 24 h (FIG. 9). At pH 10.0 and 60° C., the quantitative reaction time of cysteine with SBSeD-F or SBThD-F was attained at more than 8 h, whereas the complete reaction was achieved with SBD-F within 1 h (FIG. 10).

The water soluble fluorescent reagents SBSeD-F and SBThD-F thus presented afforded different features in terms of fluorescence properties and hydrophilicity compared with SBD-F and could be used as novel fluorescence reagents for the examination in the field of proteom analysis.

Example 10

Derivatization and Identification of *C. elegans* Protein with DAABD-Cl (1) Method

*C. elegans* (strain Bristol N2) was grown on NGM agar, using the OP50 strain of *Escherichia coli* as a food source at 20 and separated from bacteria by flotation on M9 buffer. After mashing with M9 buffer twice, the worms were stored at −80° until use. Then, they were suspended with an equal volume of 10 mM CHAPS and lysed by sonication. The soluble fraction was collected by centrifugation at 10,000 rpm for 5 min at 4° C. The supernatant was stocked as a soluble fraction at −20° C. Protein concentration of the fraction was determined by the Bradford method using BSA as a standard. About 20 μl (100 μg of protein) if the supernatant was mixed with the same volume of the respective 2.5 mM TCEP, 17.5 mM DAABD-Cl, 10 mM $Na_2EDTA$, and 50 mM CHAPS in 100 mM borate buffer (pH9.0) containing 6.0 M quanidine. After the reaction mixture was incubated at 40° C. for 30 min, the reaction was stopped with 200 μL of 0.1% formic acid, and then a 30 μL aliquot of the reaction mixture (10 μg of protein) was injected into the HPLC system.

HPLC was performed using a column of RP for PROTEIN (30 nm pore size, 250×4.6 mm i.d.) (Imtak), mobile phase is eluent (A) 0.1% trifluoroacetic acid and the eluent (B) water/$CH_3CN$/trifluoroacetic acid 70/30/0.1), the gradient system was from 70 to 30% B over 100 min with a flow rate of 0.25 mL/min. Fluorescent detection was performed at 508 nm with excitation at 387 nm. For the identification, several peak fractions of the fluorescent protein derivatives were isolated and concentrated to 10 μL under reduced pressure. Each fraction was diluted with 90 μL of 5.0 mM ammonium bicarbonate solution (pH7.8) containing 2 μg/mL trypsin and 1.0 mM calcium chloride, and the resultant mixture was incubated for 2 h at 37° C. Each ploteolytic peptide mixture was directly subjected to LC-MS/MS using an ESI ion trap mass spectrometer. Chromatography was performed using a column of HP1090 series II system and Cadenza TC-18 column (12 nm porous silica, 100×2.0 mm i.d.). Mobile phase was the eluent (A) 1.0 mM ammonium formate and eluent (B) 1.0 mM ammonium formate/$CH_3CN$ (50/50). The gradient system was from 0 to 100% over 60 min with a flow rate of 0.2 mL/min.

The identification of the protein was performed against the NCBInr database with MASCOT (Matrix Science Ltd., U.K.) database-searching algorithm memorizing the DAABD-attacged thiol residue of cysteine.

(2) Result

FIG. 11 shows a chromatogram of proteins (about 10 μg) obtained from a soluble fraction of *C. elegans* derivated with DAABD-Cl. After isolations trypsin digestion, and LC-MS/MS identification of the arbitrary selected peak fractions, we identified 10 proteins.

In the figure, 1 is ribosomal protein S3a (MW=28942), 2 is calreticulin precursor (MW=45588), 3 is ribosomal protein L 1 (MW=38635), 4 is elongation factor 1-α (MW=50636), 5 is malate dehydrogenase (MW=35098), 6 is 40S ribosomal protein (MW=22044), 7 is vitellogenin (MW=193098) 8 is arginine kinase (MW=41969) 9 is HPS-1 heat shock 70 kd protein A (MW=69680), and 10 is ribosomal protein L7Ae (MW=13992). Although, in the present experiment, only arbitrary selected 10 proteins were identified, the better separation on an elaborate column could enable identification of more proteins in a single run of the derivatization procedure.

Example 11

7-Chloro-N-(2-dimethylaminopropyle)-2,1,3-benzoxadiazole-4-sulfonamide

4-Chloro-7-chlorosulfonyl-2,1,3-benzoxadiazole (0.25 g, 0.99 mmol) was dissolved in acetonitrile (8 ml) and stirred at rt. Then, N,N-diethylethylenediamine (0.21 ml, 1.49 mmol) and triethylamine (0.21 ml, 1.49 ml) were added. The reaction mixture was stirred for 30 minutes, then concentrated in vacuo. The resulting residue was dissolved in chloroform and washed with saturated aqueous ammonium chloride and brine and organic phase was dried over $Na_2SO_4$ and concentrated in vacuo. The resulting residue was purified by silica gel column chromatography (10% methanol in chloroform) to give the product. The resulting solid was recrystallized from methylene chloride and diisopropyl to give the product as light yellow platelets (0.22 g, 0.66 mmol, 67%) $^1$H-NMR ($CDCl_3$, 500 MHz) δ7.97 (d, J=7.4 Hz, 1H), 7.53 (d, J=7.4 Hz, 1H)/3.05 (t, J=5.7 Hz, 2H), 2.48 (t, J=5.7 Hz, 2H), 2.33 (q, J=7.5 Hz, 4H), 0.87 (t, J=7.5 Hz, 6H); $^{13}$C-NMR ($CDCl_3$, 125 MHz) δ148.77, 145.00, 133.40, 129.15, 127.88, 127.47, 51.14, 46.09, 40.45, 11.36; IR(KBr, $cm^{-1}$) 3446, 3209, 3101, 2976, 2817, 1525, 1347, 1164.

Example 12

4-Chloro-7-chlorosulfonyl-2,1,3-benzoxadiazole (0.21 g, 0.88 mmol) was dissolved in acetonitrile (8 ml and stirred at 0° C. Then, N,N-diethyl-1,3-propanediamine (0.20 ml, 1.25 mmol) and triethylamine (0.17 ml, 1.25 ml) were added. The reaction mixture was stirred for 30 minutes, then concentrated in vacuo. The resulting residue was dissolved in chloroform and washed with saturated aqueous ammonium chloride and brine and the organic phase was dried over $Na_2SO_4$ and concentrated in vacuo. The resulting residue was purified by silica gel column chromatography (10% methanol in chloroform) to give the product as light yellow solid (0.10 g, 0.29 mmol, 35%) $^1$H-NMR (CD$_3$OD 500 MHz) δ8.06 (d, J=7.5 Hz, 1H), 7.77 (d, J=7.5 Hz, 1H) 3.19 (m, 8H), 1.93 (m, 2H), 1.32 (t, J=7.5 Hz, 6H); $^{13}$C-NMR (CD$_3$OD, 125 MHz) δ150.39, 146.66, 135.58, 131.33, 129.33, 128.10, 50.41, 41.21, 25.69, 9.26; IR (KBr, cm$^{-1}$) 3501, 3428, 3209, 2973, 2733, 2675, 1524, 1338, 1160.

Example 13

Synthesis of N,N-dimethylethylenediamine-d$_6$

Dimethylammonium chloride-d (2.46 g) and bromoacetonitrile (3.37 g) were dissolved in diethylether (20 ml). After addition of 50% NaOH (4.5 g) under 10° C., the mixture was stirred at the same temperature for 2 hours. The ether layer was separated and water layer was extracted with ether (10 ml×3). The combined ether layer was dried with MgSO$_4$ and then evaporated in vacuo to afford N,N-dimethylaminoacetonitrile-d$_6$ liquid solution (10 g) which was then added under 1000 to the mixture of LiAlH$_4$ (1.28 g) and sulfonic acid (1.69 g) in tetrahydrofuran (40 ml). The reaction mixture was agitated at room temperature for 13 hours. After addition of ether (30 ml), the mixture was treated with NaOH (4 g dissolved in 6 ml water). The ether layer was separated and water layer was extracted with ether (10 ml×2). The combined ether layer was dried with MgSO$_4$ and then evaporated in vacuo till the residue was reduced to 5 g. The residue was distilled and the combined fraction (70-80° C.) gave 1.79 (yield, 52.5%) of N,N-N,N-dimethylethylenediamine-d$_6$ (77.4% THF solution). $^1$H-NMR (CDCl$_3$) δ1.82-1.88 (1.54H, m for THF, 4H), 2.33 (2H, t, J=6 Hz), 2.77 (2H, t, J=6.4 Hz) 3.72-3.76 (1.48H, m for THF, 4H)

Example 14

7-chloro-4-(dimethylaminoethylaminosulfonyl)-2,1,3-benzoxaiazole-d$_6$ (DAABD-Cl-d$_6$)

4-chloro-7-chlorosulfonyle-2,1,3-benzoxadiazole (3.28 g) was dissolved in CH$_3$CN (60 ml). To this solution, N,N-dimethylethylenediamine-d$_6$ (1.0 g) and triethylamine (1.92 ml) was added successively under cooling with ice, kept standing at the same temperature for 1 hr and agitated at room temperature for 1.5 h. Then the reaction mixture was evaporated in vacuo and the resultant residue was dissolved in AcOEt. The ethyl acetate solution was washed with saturated NaHCO$_3$, distilled water, saturated NaCl solution, successively, and dried with MgSO$_4$. The filtered solution was evaporated in vacuo, and the resultant residue was purified on a silica gel column with the eluent of CH$_2$Cl$_2$:MeOH (50:1). The eluted solution was evaporated in dryness and the residue was recrystallized with EtOH-AcOEt to afford 1.36 g (yield, 41.3%) of DAABD-Cl-d6: mp, 110° C. $^1$H-NMR (CDCl$_3$): δ7.99 (1H, d, J=7.3 Hz), 7.54 (1H, d, J=7.3 Hz), 3.13 (2H, m), 2.33 (2H, m), ESI-MS: m/z 311 (M+H)$^+$, IR(KBr) cm$^{-1}$; 1342 and 1166.

Example 15

Synthesis of 7-fluoro-N-[2-(dimethylamino)ethyl]-2,1,3-benzoselenadiazole-4-sulfonamido (DAABSeD-F)

7-fluoro-2,1,3-benzoselenadiazole-4-sulfonyl chloride (75 mg) was dissolved in 3 ml of acetonitrile. After the addition of N,N-diethylethylenediamine (22 mg) and triethylamine (351), the mixture was stirred on ice for 30 min. The reaction mixture was evaporated to dryness in vacuo and the residue was dissolved in CH$_2$Cl$_2$ and chromatographed on silica gel using CH$_2$Cl$_2$-CH$_3$OH (93:7) to yield 7-fluoro-N-[2-(dimethylamino)ethyl]-2,1,3-benzoselenadiazole-4-sulfonamide (49 mg, 56%) as red powder. mp: 117-120° C. $^1$H-NMR δ$_H$8.09 (1H, d, J=7.5 Hz), 7.24 (1H, d, J=7.5 Hz), 2.93 (2H, t, J=6.7 Hz), 2.27 (2H, t, J=6.7 Hz), 1.98 (6H, s) in CD$_3$OD; ESI-MSm/z 353 [(M+H)$^+$]

Example 16

(1) Derivatization Reaction of Low Molecular Mass Thiol with DAABSeD-F and Fluorescence Properties of the Derivatives A 20 μL aliquot of 1 mM (cysteine, homocysteine, alanine, serine, tyrosine or glutathione) solution was mixed with the same volume of 2.5 mM TCEP, 17.5 mM DAABSeD-F, 10 mM Na$_9$EDTA and 50 mM CHAPS. Each reagent was dissolved in 100 mM borate buffer (pH 9.0) containing 6.0 M guanidine. The reaction mixture was heated at 40° C. for 10-120 min. and the reaction was stopped with 200 μL of 0.1% trifluoroacetic acid. The mixed solution was diluted with 300 μL of methanol and the fluorescence spectra were measured with fluorescence spectrometer. As the result, the maximum excitation of the derivative was around 420 nm, the maximum emission wavelength was around 540 nm.

(2) Separation and Identification of the DAABSeD-Derivatives of Low Molecular Mass Thiols A 10 μL of the above reaction mixture whose reaction was stopped with 0.1% trifluoroacetic acid was subjected to the HPLC system. The HPLC system consisted of a pump (L-7100, Hitach), a separation column TSK gel 120-TQA (250×4.6 mm i.d.) (Tosho) and a fluorescence detector (FL-2025, gasco). The fluorescence detection was carried out at 540 nm for the fluorescence detection and 420 nm for the excitation wavelength. The mobile phase was 150 mM phosphate buffer/CH$_3$CN (94/6), and the flow rate was 0.75 ml/min.

For the identification, the reaction mixture was directly injected to the column of a HP1090 series II system (Hewlet-Packed GmbH) with an ESI-MS to obtain MS and MS/MS spectra. Chromatography was performed on Cadenza TC-18 column (12 nm Pores of silica, 100×2.0 mm i.d.) (Imtact). Mobile phase was considered of the eluent (A) 0.1% formic acid and eluent (B) water/CH$_3$CN/formic acid (50/50/0.1). The gradient elution was carried out from 0 to 100% B over 15 min with a flow rate of 0.2 ml/min. Thus obtained chromatogram gave 3 peaks of cysteine, homocysteine and glutathione.

(3) Derivatization Reaction of Peptides and Proteins with DAABSeD-F

A 20 μL aliquot of 100 μM peptides or proteins (insulin, trysin inhibitor, α-acid glycoprotein, carbonic anhydrase or α-lactalbumin) or 10 μM BSA solution was mixed with the same volume of 2.5 mM TCEP, 17.5 mM DAABSe-Cl (as the counter part) 10 mM Na$_2$EDTA and 50 mM CHAPS. Each reagent was dissolved in 100 mM borate buffer (pH 9.0) containing 6.0 M guanidine. Each reaction mixture was heated at 40° C. for 60 min (for DAABSeD-F) or 20 min (for DAABD-Cl), and the reaction was stopped with 200 μL of 0.1% trifluoroacetic acid. The mixed solution was diluted with 300 μL of methanol and fluorescence spectra were measured with the fluorescence spectrometer. As the result, the maximum excitation was around 425 nm, the maximum fluorescence wavelength was around 535 nm.

(4) Separation of the DAASeBD-Derivative of Peptides and Proteins

Fifteen μL of the above reaction mixture without methanol was subjected to the HPLC column. The HPLC system consisted of a pump (L-7100, Hitach), a column of RP for protein (30 nm pore size, 500×4.6 i.d.) (Imtact) and a fluorescence detector (FL-202-Jasco). Fluorescence detection was carried out at 550 nm (the excitation wavelength 450 nm) (DAAB-SeD-CF) or 490 nm (the excitation wavelength 370 nm) (DAABD-Cl). The eluent (A) consisted of water/$CH_3CN$/trifluoroacetic acid (90/10/0.1) and the eluent (B) was water/$CH_3CN$/trifluoracetic acid (30/70/0.1). The gradient elution was carried out from 0 to 100% B over 200 min with a flow rate of 0.5 ml/min.

(5) HPLC Separation of the Derivatives of Peptides and Proteins with the Detection at the Different Wavelengths and Identification of Proteins A mixed solution containing α-lactalbumin, 10 mM EDTA, 50 mM CHAPS, 2.5 mM TCEP and 6.0 M guanidine was divided into two parts to prepare a sample A containing 1 μM α-lactalbumin and a sample B containing 2 μM α-lactalbumin. The sample A was reacted with DAABD-Cl at 40° C. for 20 min and the sample B was reacted with DAABSeD-F at 40° C. for 30 min, and both the reaction solution was mixed again. The mixture was subjected to HPLC-connected to the two fluorescence detectors one of which was monitored at 490 nm with excitation at 370 nm for DAABD derivatives and the other was monitored at 550 nm with excitation at 450 nm for DAABSeD derivatives. The HPLC system was the same as described above (4).

For identification of the proteins the peak fractions corresponding to the DAABD derivative of α-lactalbumin in the sample A and the DAABSeD derivative of α-lactalbumin in the sample B were combined, adjusted to pH 7.8, and digested with trypsin. Then, the resultant peptides mixture was condensed to with the blow of nitrogen gas and was subjected to HPLC-MS/MS with the probability—based protein identification algorithms MASCOT, which memorized the DAABD (MW, 3900) or DAASeBD (MW, 4539) attached thiol residue of cysteine.

Chromatography was performed using a Agilent 1100 series system (Agilent Technologies, Inc., U.S.A) and a separation columns Cadenza TC-18 column (12 nm pores of silica, 100×2.0 mm i.d.) (Imtak, Kyoto, Japan). Mobile phase consisted of the eluent (A), 0.1% formic acid and eluent (B), water/$CH_3CN$/formic acid (50/50/0.1). The gradient elution was carried out from 0 to 100% B over 60 min with a flow rate of 0.2 ml/min. As a result, α-lactalbumin (MW 16228) was identified as same as Example 10.

Example 17

(1) Sythesis of DAABSeD-F

As mentioned above, a thiol specific fluorescent reagent, 7-chloro-N-[2-(dimethylamino)ethyl]-2,1,3-benzoxadiole-4-sulfonamide (DAABD-Cl) has good sensitive and is applied successfully to proteomics studies. The emission wavelengths for the DAABD-Cl derivatized with thiols, peptides and proteins were 502 nm with the excitation wavelength of 390 nm. In this example, 7 fluoro-N-[2-(dimethylamino)ethyl]-2,1,3-benzoselenadiazole-4-sulfonamide (DAABSeD-F) was synthesized as a counterpart of DDABD-Cl by the synthesizing process in FIG. 12.

The present invention synthesized 7-fluoro-2,1,3-benzoselenadiazole-4-sulfonate (SBSeD-F) and 7-fluoro-2,1,3-benzothiadiazole-4-sulfonate (SBThD-F) as thiol specific fluorescent reagents. The fluorescent wavelengths of the reagents derivatized with cysteine were 542 nm and 517 nm with excitation at 340 nm and 315 nm, respectively. 7-fluoro-2,1,3-benzothiadiazole-4-sulfonate (SBD-F) as a benzoxazole reagent corresponding to the reagents give the derivative emitting fluorescence at 514 nm with excitation at 365 nm. The present inventor obtained a hint from the great difference of maximum wavelength between the derivatives of SBSeD-F and SBD-F and synthesized a benzoselenadiazole reagent, DAABSeD-F as a counterpart of DAABD-Cl (FIG. 12).

(2) Reaction Conditions and Reactivity of the Derivatization Reaction of DAABSeD-F for Thiol Time course studies on the derivatization reaction of small molecular mass thiols (cysteine, homocysteine, glutatione, alanine, serine and trypsin) with DAABSeD-F were performed at 40° C. (pH9.0). In case of peptides and proteins (insulin, α-acid glycoprotein, trypsin inhibitor, carbonic anhydrase, α-lactalbumin, BSA and the like), the experiment was done in the presence of CHAPS and guanidine to facilitate the reaction. As was expected, DAABSeD-F did not give any fluorescence after the reaction with none thiolic compound such as alanine containing amino and carboxyl moities) serine containing amino, carboxyl and hydroxyl moieties) and tyrosine (contain amino, carboxyl, phenolic moieties) did not yield any fluorescence after reaction. In contrast, in case of thiol compounds, the fluorescence emerged and its intensity reached maximum at 30 min, indicating that DAABSeD-F reached specifically with low molecular mass thiols as well as peptides and proteins to yield fluorescence and the reaction rate is similar to DAABD-Cl (3) Fluorescence Properties of the Derivatives with DAABSeD-F as Compared to those with DAABD-F The DAABSeD derivatives showed the maximum excitation and emission wavelengths were in the range from 423 nm to 429 nm, 524 nm to 542 nm, respectively (Table 5).

TABLE 5

| Fluorescence properties of the DAAB SeD and DAABD derivatives | | |
|---|---|---|
| | Ex(nm) | Em(nm) |
| DAABSeD Derivatives | | |
| BSA | 429 | 524 |
| Trypsin inhibitor | 423 | 536 |
| $α_1$-acid glycoprotein | 423 | 536 |
| α-lactalbmin | 426 | 534 |
| Insulin | 425 | 537 |
| Glutathioue(redused form) | 423 | 542 |
| Homocysteine | 425 | 541 |
| DAABD Derivatives | | |
| Trypsin inhibitor | 392 | 502 |
| Insulin | 393 | 502 |
| Glutathioue(redused form) | 394 | 507 |

(4) Identification and Detection of DAABSeD Derivatives of Thiols Using LC-MS

The derivatization reaction of mixtures of thiols with DAABSeD-F were subjected to HPLC with the ESI ion trap mass stectrometer. A single peak was obtained for each thiol. From the mass spectra, each DAABSeD derivate of low molecular mass thiol was detected as the base ion peaks of m/z=454 (M+H)$^+$, 468 (M+H)$^+$ and 640 (M+H)$^+$ for cysteine (MW=121), homocysteine (MW=135) and glutathione derivative (MW=307), respectively. In the present experiment, identification of DAABSeD derivatives of proteins was difficult because the limit of the molecular ion detection (less than 3,000 of MW) by the present electron spray ionization (ESI) ion trap mass spectrometer.

(5) Detection Limits for DAABSeD Derivatized Peptides and Proteins

The chromatogram obtained from the derivatives of proteins with DAABSeD-F showed a single peak for each of the derivatives, and no interfering peaks were observed. Any DAABSeD-F peak didn't appear because the reagent itself does not fluoresce. The peak heights for the derivatives above mentioned were linear against the amounts of injection. The detection limits for vasopressin, α-lactalbumin and BSA were 7.5, 7.2, and 7.2 fmol, respectively for the derivatives. These detection limits were similar to those of DAABD derivatives.

Compared to the DAABD derivatives the DAABSeD derivatives were eluted earlier, so that the DAABSeD derivatives would have less affinity to the HPLC stationary phase than the DAABD derivatives. The same trend was also observed for the SBSeD derivatives as compared to the SBD derivatives.

(6) Simultaneous Detection of DAABSeD and DAABD Derivatives

A combination of DAABD and DAABSeD derivatization, and simultaneous fluorescent detection of the two derivatives would simplify the comparison of the two protein samples of the same origin but treated with different conditions. For example, one is a sample from a patient and one is a sample from a healthy person, or the two cell culture samples, one of which was treated with some drug and the other was without treatment.

In the present experiment, the reaction solution of the DAABD derivative of α-lactalbumin in the sample A and the reaction solution of the DAASeBD derivative of α-lactalbumin in the sample B were combined and subjected to HPLC-connected to the two fluorescence detector. The respective detection wavelengths were performed at 490 nm with excitation at 370 nm for the DAABD derivatives and at 550 nm with excitation at 450 nm for DAASeBD derivatives. Both the derivatives gave each single peak on the respective chromatograms. The retention times for the DAABD derivatives of α-lactalbumin, and the DAASeBD derivatives of α-lactalbumin were 53.3 min and 50.0 min, respectively.

The DAABD derivatives of α-lactalbumin in the sample A were observed, but the DAABSeD derivatives of α-lactalbumin in the sample B were not observed, while the DAASeBD derivative of α-lactalbumin in the sample B were observed, but the DAABD derivatives of α-lactalbumin in the sample A were not observed. Thus, in this manner, we can distinguish α-lactalbumin present in the sample A from α-lactalbumin present in the sample B, and calculate and compare the amounts of either of them in both the samples.

A further treatment with a tryptic enzyme such as a trypsin of the combined mixture of the isolated corresponding peak fraction could result in the identification of the protein. For example, the peaks corresponding to the DAABD derivative of α-lactalbumin in the sample A and the DAASeBD derivative of α-lactalbumin in the sample B were combined, digested with trypsin and the resultant peptides mixture was subjected to HPLC-connected to the two fluorescence detectors to separate and calculate the protein (α-lactalbumin), further, the obtained peptides mixture was subjected to HPLC-MS/MS with probability—based protein identification algorithm, MASCOT, which memorized the DAABD or DAASeBD attached thiol residue of cysteine. As the result, n-lactalbumin (MW16228) was identified as same as the Example 10.

In the present experiment, comparison of the amount of the protein α-lactalbumin in the different samples A and B. On the contrary, the real bio-sample, where there are many compounds present in one sample, the combined mixture of the derivatized protein solution gave a complex pattern of HPLC chromatogram, and thus it should be very difficult to distinguish the protein peaks on the chromatogram. However, if the authentic standard of the target protein is available and different chromatographic conditions for protein are available, we can know the retentions of the two derivatives of the protein on the two chromatography. Then, after the isolation of the peak fractions of either derivative with DAABD-Cl and DAASeBD-F on one chromatogram, the combined peak fraction could be re-chromatographed on the second chromatography to calculate the purified each derivative of the protein. Further the peak fractions are subjected to the above mentioned enzymatic treatment, fluorescence detection HPLC or LC-Mas analyser to calculate and identify the amount of the protein in the different samples.

INDUSTRIAL APPLICABILITY

As has been described in detail above, the present invention relates to a method and system for detecting, separating and identifying trace expressed protein and/or peptide. According to the present invention, protein and/or peptide expressed through a gene can be detected separated and identified with high sensitivity using a simple method and means. According to the method of the present invention, trace expressed protein and/or peptide unable to be detected with methods of the prior art can be detected, separated and identified with high sensitivity and in a short period of time. In addition, the present invention is also able to provide a system for detecting, separating and identifying trace amounts of trace expressed protein and/or peptide used in the above-mentioned detection, separation and identification method. The present invention is useful for providing proteome platform technology.

Figure 1:
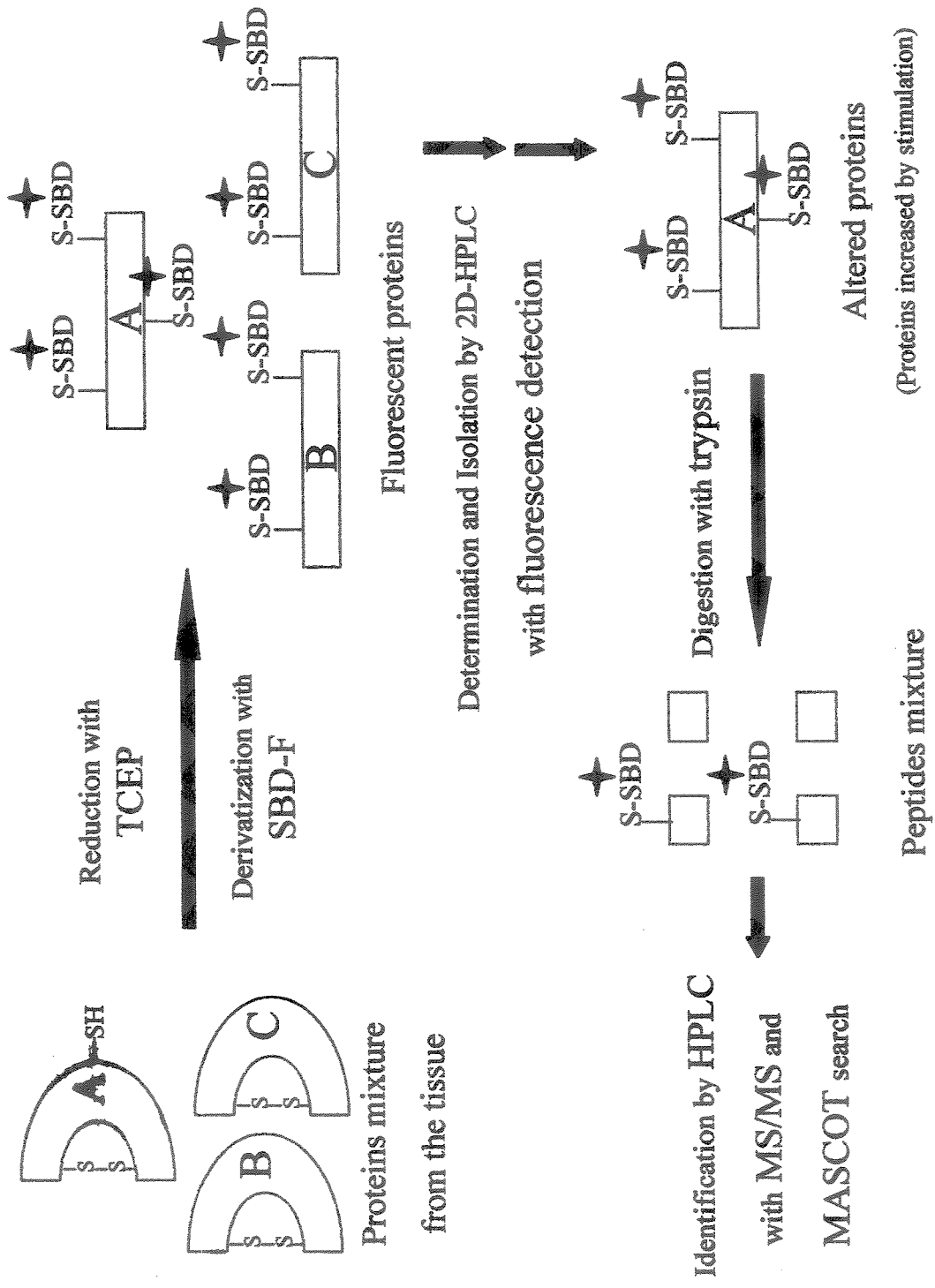
FIG. 1 shows an example of the procedure for the method of the present invention.
Figure 2:
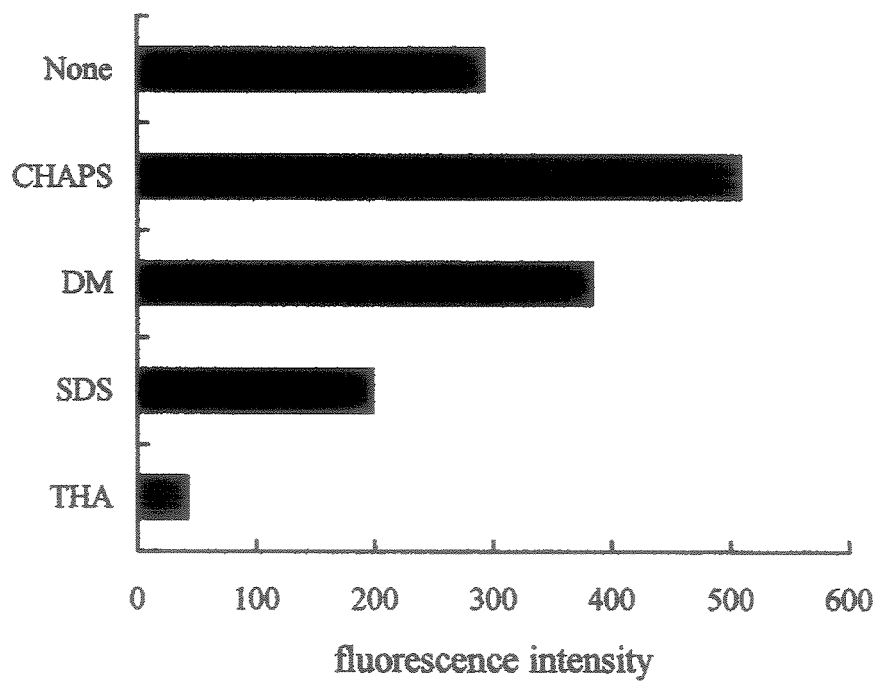
FIG. 2 shows the relationship between the type of surfactant and the degree of fluorescent derivative formation.
Figure 3:
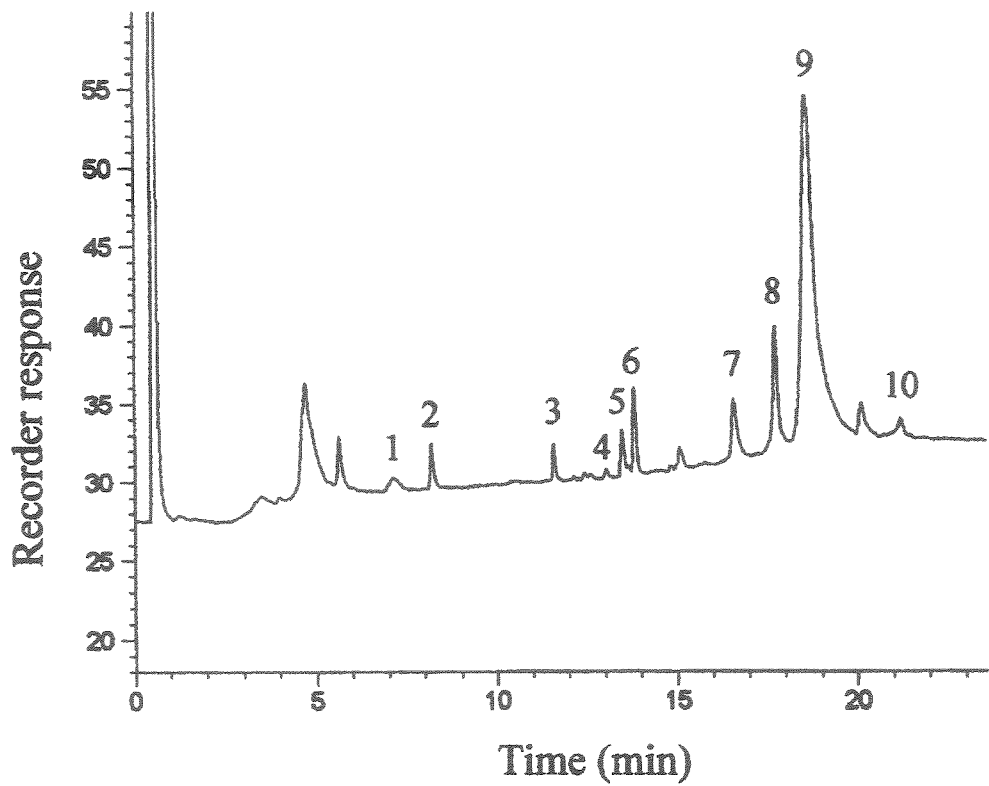
FIG. 3 shows the respective fluorescence peaks of fluorescent derivative protein/peptide tested according to the method of the present invention.
Figure 4:
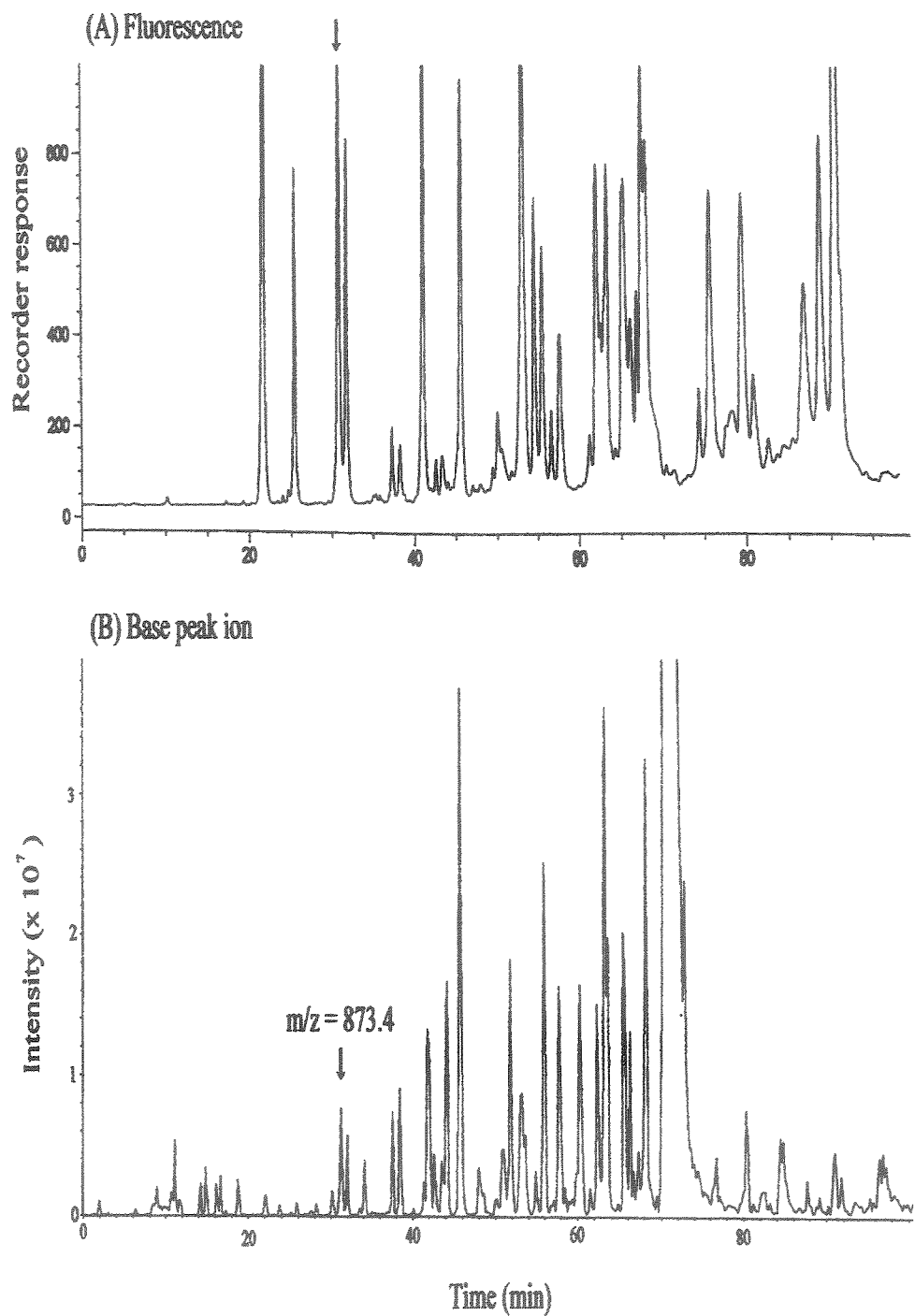
FIG. 4 shows a fluorescence chromatogram (A) and fluorescence chromatogram (B) of an enzymatic hydrolysis product.
Figure 5:
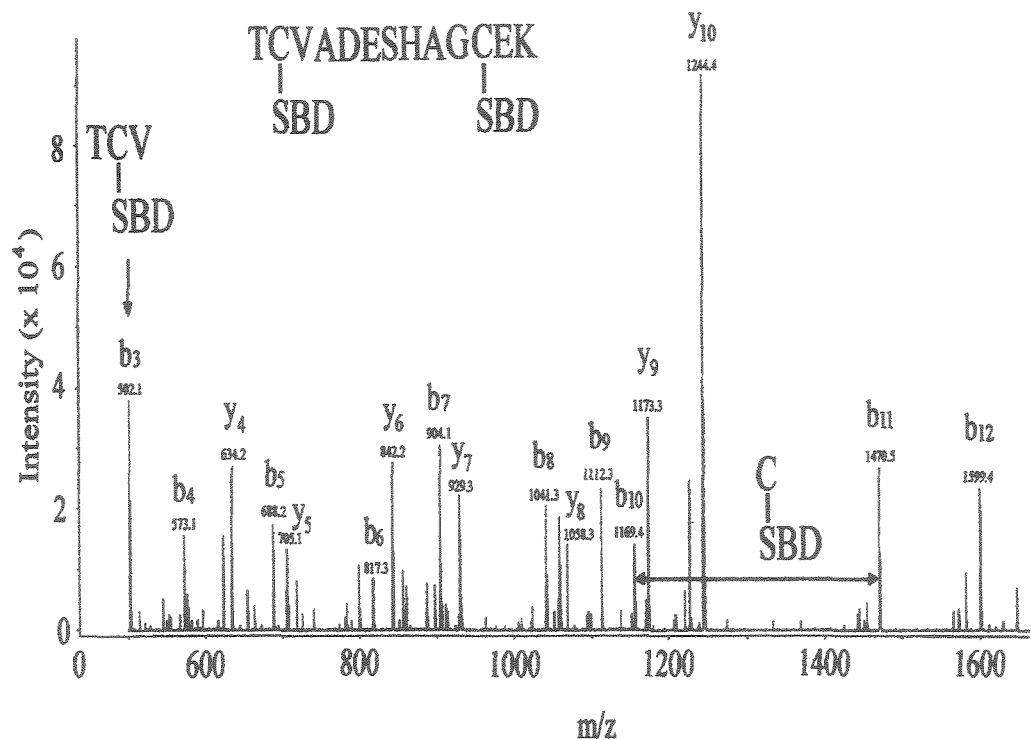
FIG. 5 shows a spectrum obtained by MS/MS.
Figure 6:
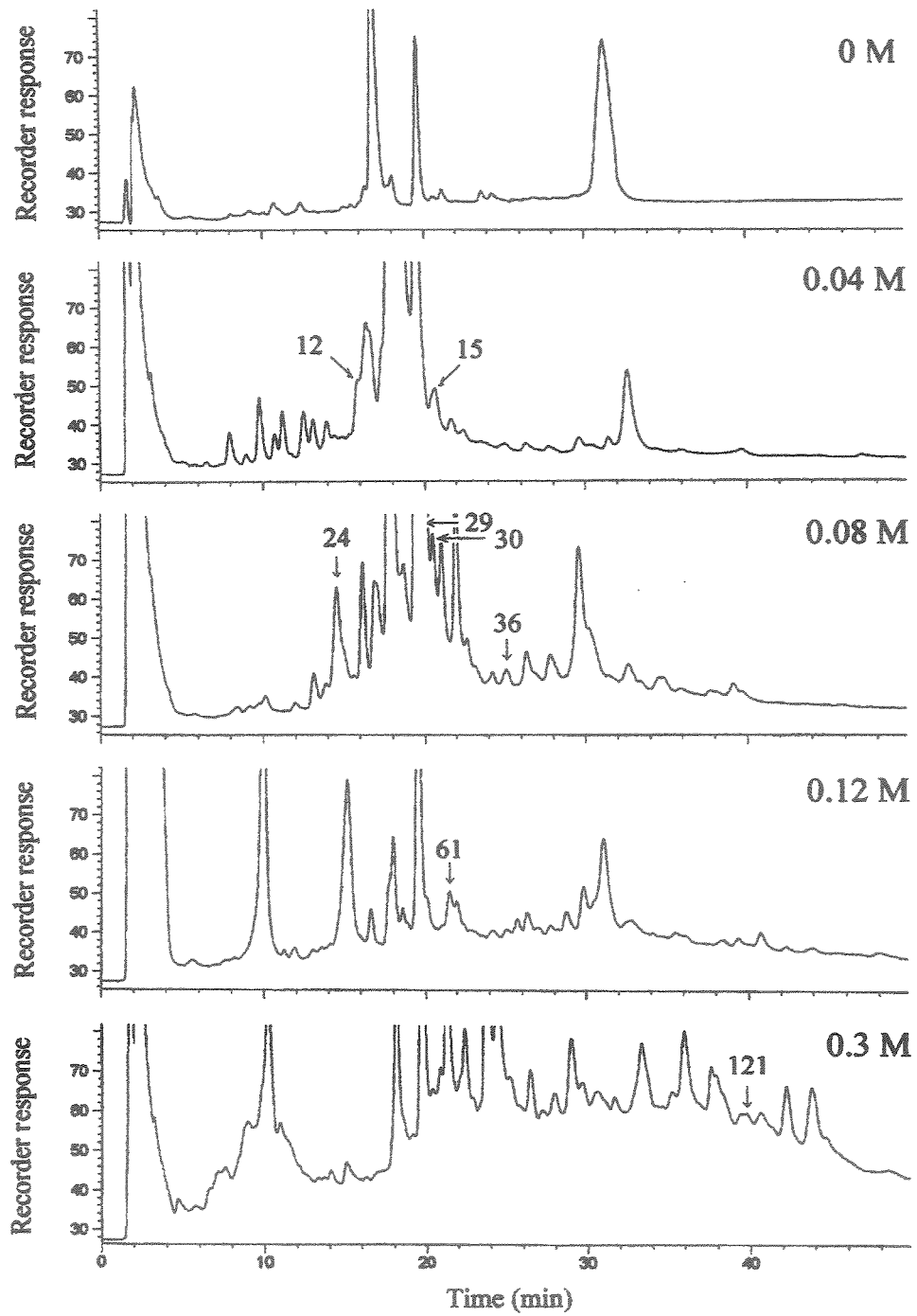
FIG. 6 shows chromatograms obtained by reverse phase chromatography (RPLC) in Example 3.
Figure 7:
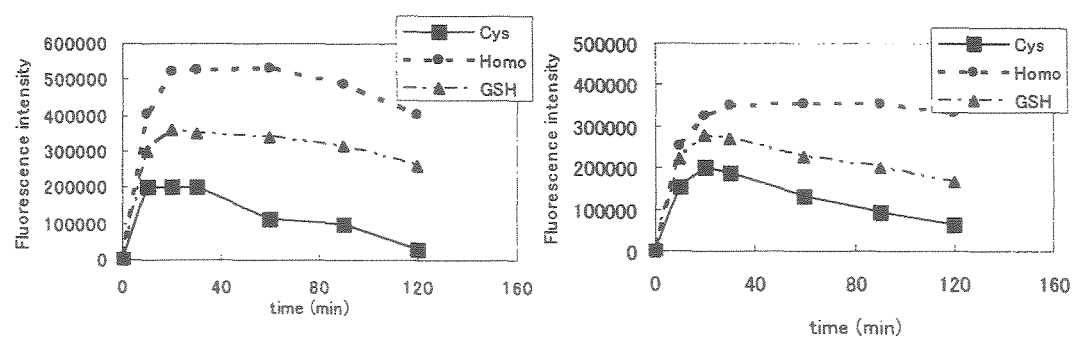
FIG. 7 shows the relationship between the reaction time and fluorescence intensity of fluorescent derivatization (left: DAABD-Cl, right: TAABD-Cl)
Figure 8:
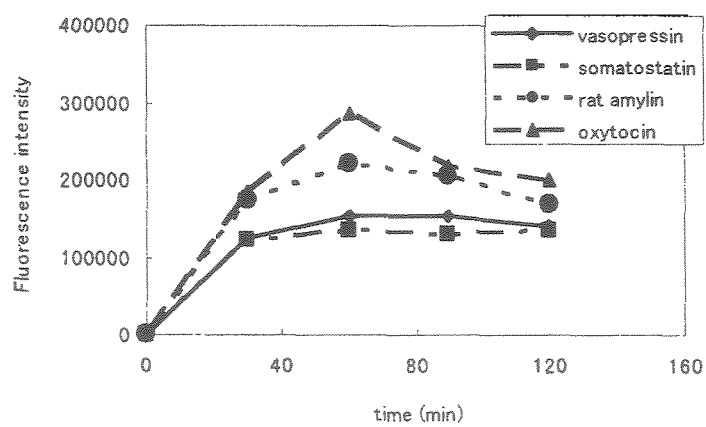
FIG. 8 shows the relationship between reaction time and fluorescence intensity for TAABD-1.
Figure 9:
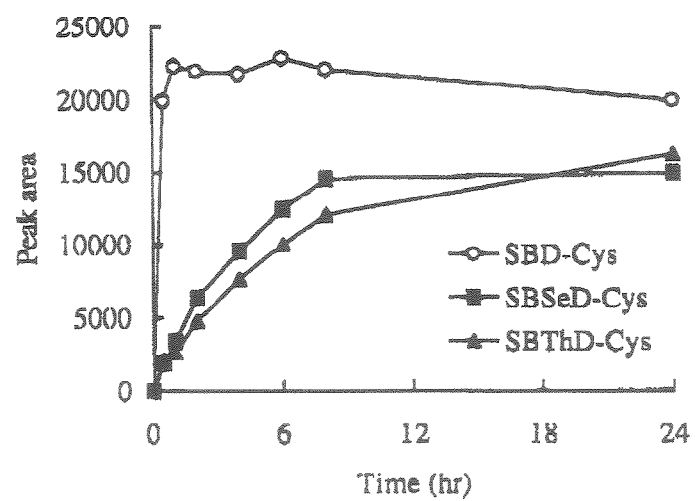
FIG. 9 shows the relationship between reaction time and peak area of fluorescent derivatization of cysteine using a novel fluorescence reagent (pH 9.0)
Figure 10:
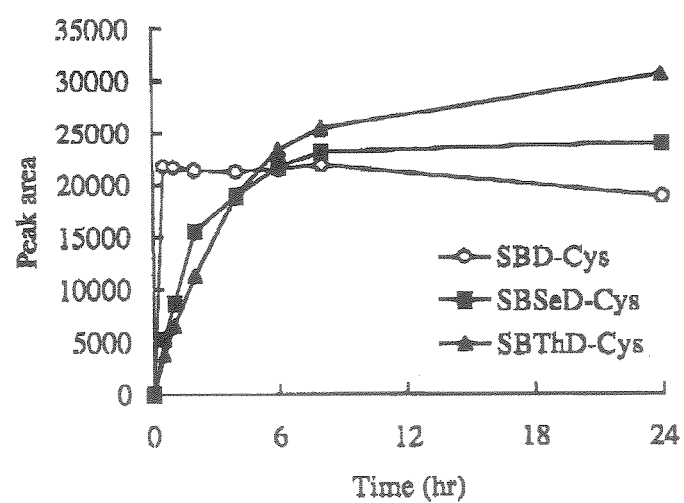
FIG. 10 shows the relationship between reaction time and peak area of the fluorescent derivatization of cysteine using a novel fluorescence reagent (pH 10.0)
Figure 11:
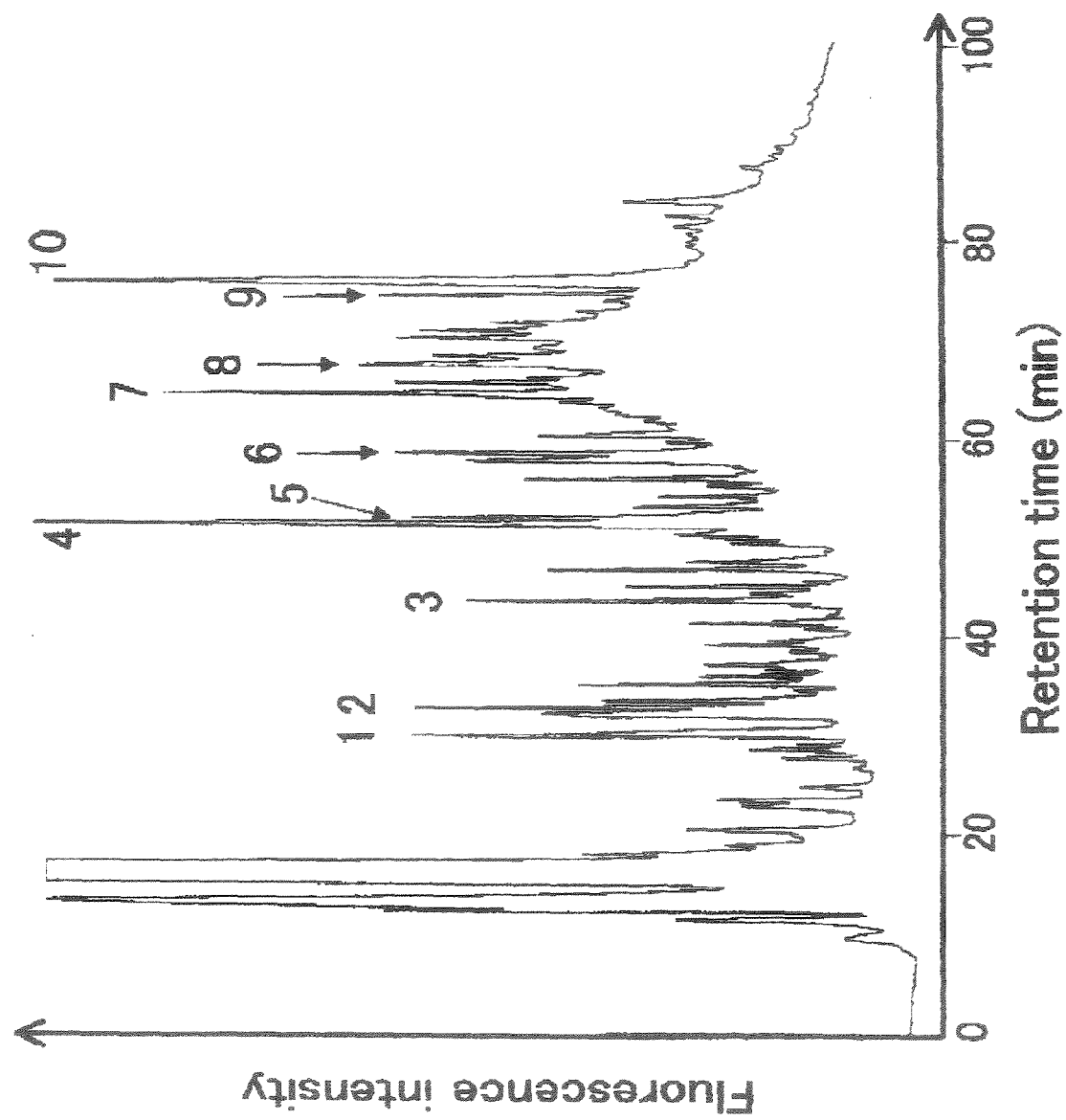
FIG. 11 shows the chromatogram of a protein obtained from the soluble fraction of a nematode (*C. elegans*) derivatized with DAABD-Cl.
Figure 12:
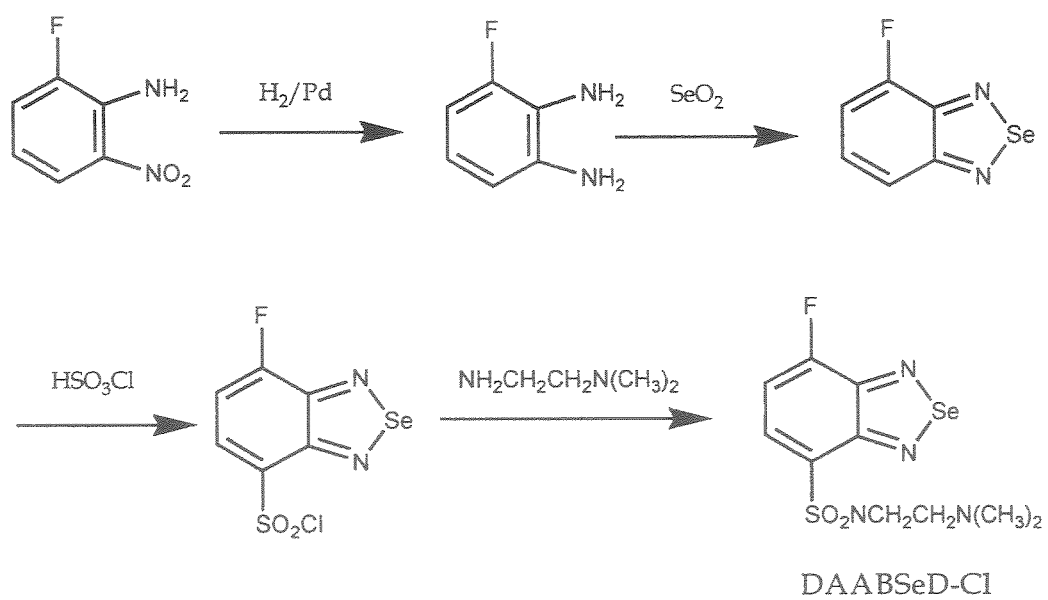
FIG. 12 shows the synthesis pathway of DAASeD-X.

The invention claimed is:

1. A method for detecting, separating and identifying an expressed trace protein and/or peptide in a test sample, comprising:
    converting a protein and/or peptide in a test sample to a fluorescent derivative by labeling said protein and/or peptide with a fluorescent derivatization reagent, wherein said fluorescent derivatization reagent, which does not fluoresce itself, is one selected from the group consisting of DAABD-X, TAABD-X, DAABSeD-X, TAABSeD-X, DAABThD-X, and TAABThD-X, wherein X represents Cl or F
    subjecting the labeled protein and/or peptide to one-dimensional or two-dimensional HPLC/fluorescence detection, to obtain fluorescent fractions,
    applying the fluorescent fractions to enzymatic hydrolysis to obtain digested peptide fragments,
    subjecting the digested peptide fragments to second stage HPLC/fluorescence detection to obtain a fluorescent chromatogram,
    applying peptide fractions of the fluorescent chromatogram to mass spectrometry or MS/MS analysis,
    collating the mass spectrometry or MS/MS data with a database, and
    providing said collated data for structural analysis to identify the expressed protein and/or peptide.

2. The method according to claim 1, wherein a functional group-specific fluorescent derivatization reagent is added to an aqueous solution of the protein and/or peptide sample, and a surfactant and/or protein denaturing agent is optionally added, to fluorescently label the protein and/or peptide.

3. The method according to claim 1, wherein the fluorescent derivative is applied to a separation means of a HPLC/fluorescence detection selected from the group consisting of an ion exchange column HPLC equipped with a fluorescence detector, a reverse phase partition HPLC equipped with a fluorescence detector, a gel filtration HPLC equipped with a fluorescence detector, and a peak fraction thereof is captured while monitoring fluorescence.

4. The method according to claim 1, wherein the fluorescent fraction is applied to enzymatic hydrolysis using a protease selected from the group consisting of a peptidase, a trypsin and a chymotrypsin.

5. The method according to claim 1, wherein the digested peptide fragments are applied to reverse phase HPLC equipped with a fluorescence detector to detect a fluorescence peak, and mass spectrometry or MS/MS analysis is carried out on fluorescence-labeled fragments and non-fluorescence-labeled fragments.

6. The method according to claim 1, wherein the test sample is a protein and/or peptide sample collected from a biological sample.

7. A method for detecting, separating and identifying a protein and/or peptide, comprising
    converting a protein and/or peptide in different test samples in the form of sample A and sample B to a fluorescent derivative, respectively, with at least two fluorescent derivatization reagents, wherein said fluorescent derivation derivatization reagents do not fluoresce themselves and have different fluorescence wavelengths,
    separating and detecting the fluorescent derivative with an HPLC equipped with a fluorescence detector,
    applying each fluorescence peak either directly or collectively to enzymatic hydrolysis, and
    applying the hydrolysis product to HPLC-mass spectrometry,
    wherein the protein and/or peptide is converted to a derivative with at least two fluorescent derivatization reagents selected from the group consisting of DAABD-X, DAABSeD-X, DAABThD-X, an isotope of DAABD-X, an isotope of DAABSeD-X, and an isotope of DAABThD-X, wherein X represents Cl or F.

8. The method according to claim 7, wherein each fluorescence peak is applied to quantification by HPLC either directly or collectively, and the ratio of each derivative of the protein and/or peptide in sample A and sample B is calculated.

9. The method according to claim 7, wherein the hydrolysis product is applied to quantification by HPLC, and the ratio of each derivative of the protein and/or peptide in sample A and sample B is calculated.

10. The method according to claim 7, wherein the reaction product of a first fluorescent derivatization reagent and the reaction product of a second fluorescent derivatization reagent with the protein and/or peptide in sample A and sample B are combined, applied to HPLC capable of excitation and fluorescence detection, applied to enzymatic hydrolysis after fractionating and combining each fluorescence peak, and identification is carried out by applying the hydrolysis product to HPLC-mass spectrometry.

11. The method according to claim 7, wherein samples A and B are two types of cell, tissue or body fluid samples.

* * * * *